US011260136B2

(12) United States Patent
Linden et al.

(10) Patent No.: US 11,260,136 B2
(45) Date of Patent: Mar. 1, 2022

(54) RADIO-PHARMACEUTICAL COMPLEXES

(71) Applicants: BAYER PHARMA AKTIENGESELLSCHAFT, Berlin (DE); Bayer AS, Oslo (NO)

(72) Inventors: Lars Linden, Gevelsberg (DE); Alan Cuthbertson, Oslo (NO)

(73) Assignees: BAYER PHARMA AKTIENGESELLSCHAFT, Berlin (DE); Bayer AS, Oslo (NO)

( * ) Notice: Subject to any disclaimer, the term of this patent is extended or adjusted under 35 U.S.C. 154(b) by 0 days.

(21) Appl. No.: 16/087,040

(22) PCT Filed: Mar. 20, 2017

(86) PCT No.: PCT/EP2017/056503
§ 371 (c)(1),
(2) Date: Sep. 20, 2018

(87) PCT Pub. No.: WO2017/162555
PCT Pub. Date: Sep. 28, 2017

(65) Prior Publication Data
US 2019/0091354 A1 Mar. 28, 2019

(30) Foreign Application Priority Data
Mar. 24, 2016 (EP) .................... 16162123

(51) Int. Cl.
*A61K 51/08* (2006.01)
*A61K 51/06* (2006.01)
*A61K 51/10* (2006.01)
*C07K 16/32* (2006.01)

(52) U.S. Cl.
CPC ........ *A61K 51/1093* (2013.01); *A61K 51/103* (2013.01); *A61K 51/1051* (2013.01); *A61K 51/1054* (2013.01); *A61K 51/1063* (2013.01); *A61K 51/1072* (2013.01); *A61K 51/1096* (2013.01); *C07K 16/32* (2013.01)

(58) Field of Classification Search
CPC ................ A61K 38/00; A61K 2121/00; A61K 2123/00; A61K 51/00; A61K 51/08; A61K 51/1093; A61K 51/103; A61K 51/1054; A61K 51/1072; A61K 51/1063; A61K 51/1096; A61K 51/06; A61K 51/088; A61K 51/1051; C07K 16/32
USPC ........ 424/1.11, 1.65, 1.69, 9.1, 9.2, 9.3, 9.4, 424/9.5, 9.6; 514/1, 1.1, 19.2, 19.3, 19.4, 514/19.5, 19.6; 534/7, 10–16; 530/300
See application file for complete search history.

(56) References Cited

U.S. PATENT DOCUMENTS

| 7,794,691 B2 * | 9/2010 | Morgenstern | A61K 51/1045 424/1.11 |
| 9,724,436 B2 * | 8/2017 | Ramdahl | A61K 51/1051 |
| 10,682,430 B2 * | 6/2020 | Ramdahl | A61K 51/1051 |

FOREIGN PATENT DOCUMENTS

| WO | WO-2011/098611 | 8/2011 |
| WO | WO-2013/167756 | 11/2013 |
| WO | WO-2016/096843 | 6/2016 |

OTHER PUBLICATIONS

Heyerdahl, et al., (Aug. 2012) "Fractionated Therapy of HER2-Expressing Breast and Ovarian Cancer Xenografts in Mice with Targeted Alpha Emitting $^{227}$Th-DOTA-p-benzyl-trastuzumab," PLoS ONE, 7(8):1-14.

* cited by examiner

*Primary Examiner* — D. L. Jones
(74) *Attorney, Agent, or Firm* — Morrison & Foerster LLP

(57) ABSTRACT

The invention provides a method for the formation of a tissue-targeting thorium complex, said method comprising; a) forming an octadentate chelator comprising four hydroxypyridinone (HOPO) moieties, substituted in the N-position with a methyl group, and a coupling moiety terminating in a carboxylic acid group; b) coupling said octadentate chelator to at least one tissue-targeting moiety targeting HER2; and c) contacting said tissue-targeting chelator with an aqueous solution comprising an ion of at least one alpha-emitting thorium isotope. A method of treatment of a neoplastic or hyperplastic disease comprising admistration of such a tissue-targeting thorium complex, as well as the complex and corresponding pharmaceutical formulations are also provided.

9 Claims, No Drawings

Specification includes a Sequence Listing.

SEQUENCE LISTING

<160> NUMBER OF SEQ ID NOS: 6

<210> SEQ ID NO 1
<211> LENGTH: 214
<212> TYPE: PRT
<213> ORGANISM: Artificial Sequence
<220> FEATURE:
<223> OTHER INFORMATION: Light Chain

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 449
<212> TYPE: PRT
<213> ORGANISM: Artificial Sequence
<220> FEATURE:
<223> OTHER INFORMATION: Heavy Chain Seq 2

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

-continued

```
Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 3
<211> LENGTH: 449
<212> TYPE: PRT
<213> ORGANISM: Artificial Sequence
<220> FEATURE:
<223> OTHER INFORMATION: Heavy Chain Seq 3
```

```
<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 4
<211> LENGTH: 449
<212> TYPE: PRT
<213> ORGANISM: Artificial Sequence
<220> FEATURE:
<223> OTHER INFORMATION: Heavy Chain Seq 4

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
        100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 5
<211> LENGTH: 449
<212> TYPE: PRT
<213> ORGANISM: Artificial Sequence
<220> FEATURE:
<223> OTHER INFORMATION: Heavy Chain Seq 4

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
```

```
                225                 230                 235                 240
        Pro Ser Val Phe Leu Phe Pro Lys Pro Lys Asp Thr Leu Met Ile
                    245                 250                 255

Ser Arg Thr Pro Glu Val Thr Cys Val Val Val Asp Val Ser His Glu
                    260                 265                 270

Asp Pro Glu Val Lys Phe Asn Trp Tyr Val Asp Gly Val Glu Val His
                    275                 280                 285

Asn Ala Lys Thr Lys Pro Arg Glu Glu Gln Tyr Gln Ser Thr Tyr Arg
            290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Ala Pro Ile Glu
                        325                 330                 335

Lys Thr Ile Ser Lys Ala Lys Gly Gln Pro Arg Glu Pro Gln Val Tyr
                    340                 345                 350

Thr Leu Pro Pro Ser Arg Asp Glu Leu Thr Lys Asn Gln Val Ser Leu
                    355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                        405                 410                 415

Lys Ser Arg Trp Gln Gln Gly Asn Val Phe Ser Cys Ser Val Met His
                    420                 425                 430

Glu Ala Leu His Asn His Tyr Thr Gln Lys Ser Leu Ser Leu Ser Pro
                    435                 440                 445

Gly

<210> SEQ ID NO 6
<211> LENGTH: 449
<212> TYPE: PRT
<213> ORGANISM: Artificial Sequence
<220> FEATURE:
<223> OTHER INFORMATION: Heavy Chain Seq 6

<400> SEQUENCE: 6

Glu Val Gln Leu Val Glu Ser Gly Gly Gly Leu Val Gln Pro Gly Gly
        1               5                   10                  15

Ser Leu Arg Leu Ser Cys Ala Ala Ser Gly Phe Asn Ile Lys Asp Thr
                    20                  25                  30

Tyr Ile His Trp Val Arg Gln Ala Pro Gly Lys Gly Leu Glu Trp Val
                    35                  40                  45

Ala Arg Ile Tyr Pro Thr Asn Gly Tyr Thr Arg Tyr Ala Asp Ser Val
            50                  55                  60

Lys Gly Arg Phe Thr Ile Ser Ala Asp Thr Ser Lys Asn Thr Ala Tyr
        65                  70                  75                  80

Leu Gln Met Asn Ser Leu Arg Ala Glu Asp Thr Ala Val Tyr Tyr Cys
                        85                  90                  95

Ser Arg Trp Gly Gly Asp Gly Phe Tyr Ala Met Asp Tyr Trp Gly Gln
                    100                 105                 110

Gly Thr Leu Val Thr Val Ser Ser Ala Ser Thr Lys Gly Pro Ser Val
                    115                 120                 125

Phe Pro Leu Ala Pro Ser Ser Lys Ser Thr Ser Gly Gly Thr Ala Ala
                130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Asn Tyr Gln Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly
```

RADIO-PHARMACEUTICAL COMPLEXES

CROSS REFERENCE TO RELATED APPLICATIONS

This application is a National Phase application under 35 U.S.C. § 371 of International Application No. PCT/EP2017/056503, filed Mar. 20, 2017, which claims priority benefit of European Application No. 16162123.0, filed Mar. 24, 2016.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052024200SEQLIST.TXT, date recorded: Sep. 18, 2018, size: 21 KB).

FIELD OF THE INVENTION

The present invention relates to methods for the formation of complexes of thorium-227 with certain octadentate ligands conjugated to a tissue targeting moiety targeting the HER2 antigen. The invention also relates to the complexes, and to the treatment of diseases, particularly neoplastic diseases, involving the administration of such complexes.

BACKGROUND TO THE INVENTION

Specific cell killing can be essential for the successful treatment of a variety of diseases in mammalian subjects. Typical examples of this are the treatment of malignant diseases such as sarcomas and carcinomas. However the selective elimination of certain cell types can also play a key role in the treatment of other diseases, especially hyperplastic and neoplastic diseases.

The most common methods of selective treatment are currently surgery, chemotherapy and external beam irradiation. Targeted radionuclide therapy is, however, a promising and developing area with the potential to deliver highly cytotoxic radiation specifically to cell types associated with disease. The most common forms of radiopharmaceuticals currently authorised for use in humans employ beta-emitting and/or gamma-emitting radionuclides. There has, however, been some interest in the use of alpha-emitting radionuclides in therapy because of their potential for more specific cell killing.

The radiation range of typical alpha emitters in physiological surroundings is generally less than 100 micrometers, the equivalent of only a few cell diameters. This makes these sources well suited for the treatment of tumours, including micrometastases, because they have the range to reach neighbouring cells within a tumour but if they are well targeted then little of the radiated energy will pass beyond the target cells. Thus, not every cell need be targeted but damage to surrounding healthy tissue may be minimised (see Feinendegen et al., Radiat Res 148:195-201 (1997)). In contrast, a beta particle has a range of 1 mm or more in water (see Wilbur, Antibody Immunocon Radiopharm 4: 85-96 (1991)).

The energy of alpha-particle radiation is high in comparison with that carried by beta particles, gamma rays and X-rays, typically being 5-8 MeV, or 5 to 10 times that of a beta particle and 20 or more times the energy of a gamma ray. Thus, this deposition of a large amount of energy over a very short distance gives α-radiation an exceptionally high linear energy transfer (LET), high relative biological efficacy (RBE) and low oxygen enhancement ratio (OER) compared to gamma and beta radiation (see Hall, "Radiobiology for the radiologist", Fifth edition, Lippincott Williams & Wilkins, Philadelphia Pa., USA, 2000). This explains the exceptional cytotoxicity of alpha emitting radionuclides and also imposes stringent demands on the biological targeting of such isotopes and upon the level of control and study of alpha emitting radionuclide distribution which is necessary in order to avoid unacceptable side effects.

So far, with regards to the application in radioimmunotherapy the main attention has been focused on $^{211}$At, $^{213}$Bi and $^{225}$AC and these three nuclides have been explored in clinical immunotherapy trials.

Several of the radionuclides which have been proposed are short-lived, i.e. have half-lives of less than 12 hours. Such a short half-life makes it difficult to produce and distribute radiopharmaceuticals based upon these radionuclides in a commercial manner. Administration of a short-lived nuclide also increases the proportion of the radiation dose which will be emitted in the body before the target site is reached.

The recoil energy from alpha-emission will in many cases cause the release of daughter nuclides from the position of decay of the parent. This recoil energy is sufficient to break many daughter nuclei out from the chemical environment which may have held the parent, e.g. where the parent was complexed by a ligand such as a chelating agent. This will occur even where the daughter is chemically compatible with, i.e. complexable by, the same ligand. Equally, where the daughter nuclide is a gas, particularly a noble gas such as radon, or is chemically incompatible with the ligand, this release effect will be even greater. When daughter nuclides have half-lives of more than a few seconds, they can diffuse away into the blood system, unrestrained by the complexant which held the parent. These free radioactive daughters can then cause undesired systemic toxicity.

The use of Thorium-227 ($T_{1/2}$=18.7 days) under conditions where control of the $^{223}$Ra daughter isotope is maintained was proposed a few years ago (see WO 01/60417 and WO 02/05859). This was in situations where a carrier system is used which allows the daughter nuclides to be retained by a closed environment. In one case, the radionuclide is disposed within a liposome and the substantial size of the liposome (as compared to recoil distance) helps retain daughter nuclides within the liposome. In the second case, bone-seeking complexes of the radionuclide are used which incorporate into the bone matrix and therefore restrict release of the daughter nuclides. These are potentially highly advantageous methods, but the administration of liposomes is not desirable in some circumstances and there are many diseases of soft tissue in which the radionuclides cannot be surrounded by a mineralised matrix so as to retain the daughter isotopes.

More recently, it was established that the toxicity of the $^{223}$Ra daughter nuclei released upon decay of $^{227}$Th could be tolerated in the mammalian body to a much greater extent than would be predicted from prior tests on comparable nuclei. In the absence of the specific means of retaining the radium daughters of thorium-227 discussed above, the publicly available information regarding radium toxicity made it clear that it was not possible to use thorium-227 as a therapeutic agent since the dosages required to achieve a therapeutic effect from thorium-227 decay would result in a highly toxic and possibly lethal dosage of radiation from the decay of the radium daughters, i.e. there is no therapeutic window.

WO 04/091668 describes the unexpected finding that a therapeutic treatment window does exist in which a therapeutically effective amount of a targeted thorium-227 radionuclide can be administered to a subject (typically a mammal) without generating an amount of radium-223 sufficient to cause unacceptable myelotoxicity. This can therefore be used for treatment and prophylaxis of all types of diseases at both bony and soft-tissue sites.

In view of the above developments, it is now possible to employ alpha-emitting thorium-227 nuclei in endoradionuclide therapy without lethal myelotoxicity resulting from the generated $^{223}$Ra. Nonetheless, the therapeutic window remains relatively narrow and it is in all cases desirable to administer no more alpha-emitting radioisotope to a subject than absolutely necessary. Useful exploitation of this new therapeutic window would therefore be greatly enhanced if the alpha-emitting thorium-227 nuclei could be complexed and targeted with a high degree of reliability.

Because radionuclides are constantly decaying, the time spent handling the material between isolation and administration to the subject is of great importance. It would also be of considerable value if the alpha-emitting thorium nuclei could be complexed, targeted and/or administered in a form which was quick and convenient to prepare, preferably requiring few steps, short incubation periods and/or temperatures not irreversibly affecting the properties of the targeting entity. Furthermore, processes which can be conducted in solvents that do not need removal before administration (essentially in aqueous solution) have the considerable advantage of avoiding a solvent evaporation or dialysis step.

It would also be considered of significant value if a thorium labelled drug product formulation could be developed which demonstrated significantly enhanced stability. This is critical to ensure that robust product quality standards are adhered to while at the same time enabling a logistical path to delivering patient doses. Thus formulations with minimal radiolysis over a period of 1-4 days are preferred.

Octadentate chelating agents containing hydroxypyridinone groups have previously been shown to be suitable for coordinating the alpha emitter thorium-277, for subsequent attachment to a targeting moiety (WO2011098611). Octadentate chelators were described, containing four 3,2-hydroxypyridinone groups joined by linker groups to an amine-based scaffold, having a separate reactive group used for conjugation to a targeting molecule. Preferred structures of the previous invention contained 3,2-hydroxypyridinone groups and employed the isothiocyanate moiety as the preferred coupling chemistry to the antibody component as shown in compound ALG-DD-NCS. The isothiocyanate is widely used to attach a label to proteins via amine groups. The isothiocyanate group reacts with amino terminal and primary amines in proteins and has been used for the labelling of many proteins including antibodies. Although the thiourea bond formed in these conjugates is reasonably stable, it has been reported that antibody conjugates prepared from fluorescent isothiocyanates deteriorate over time. [Banks P R, Paquette D M, Bioconjug Chem (1995) 6:447-458]. The thiourea formed by the reaction of fluorescein isothiocyanate with amines is also susceptible to conversion to a guanidine under basic conditions [Dubey I, Pratviel G, Meunier BJournal: Bioconjug Chem (1998) 9:627-632]. Due to the long decay half-life of thorium-227 (18.7 days) coupled to the long biological half-life of a monoclonal antibody it is desirable to use more stable linking moieties so as to generate conjugates which are more chemically stable both in vivo and to storage.

The most relevant previous work on conjugation of hydroxypyridinone ligands was published in WO2013/167754 and discloses ligands possessing a water solubilising moiety comprising a hydroxyalkyl functionality. Due to the reactivity of the hydroxyl groups of this chelate class activation as an activated ester is not possible as multiple competing reactions ensue leading to a complex mixture of products through esterification reactions. The ligands of WO2013/167754 must therefore be coupled to the tissue-targeting protein via alternative chemistries such as the isothiocyanate giving a less stable thiourea conjugate as described above. In addition WO2013167755 and WO2013167756 discloses the hydroxyalkyl/isothiocyanate conjugates applied to CD33 and CD22 targeted antibodies respectively.

The HER family of receptor tyrosine kinases are important mediators of cell growth, differentiation and survival. The receptor family includes four distinct members including epidermal growth factor receptor (EGFR, ErbB1, or HER1), HER2 (ErbB2 or p185$^{neu}$), HER3 (ErbB3) and HER4 (ErbB4 or tyro2).

Overexpression of HER2 (frequently but not uniformly due to gene amplification) has been observed in carcinomas including carcinomas of the stomach, endometrium, salivary gland, Jung, kidney, colon, thyroid, pancreas and bladder.

HER2 is the target of the monoclonal antibody trastuzumab. Trastuzumab received marketing approval from the Food and Drug Administration Sep. 25, 1998 for the treatment of patients with metastatic breast cancer whose tumors overexpress the HER2 protein. Methods for making trastuzumab are disclosed in WO92/22653.

The present inventors have now established that by forming a tissue targeting complex by coupling specific chelators to a monoclonal antibody to HER2 as the targeting moiety, followed by addition of an alpha-emitting thorium ion, a complex may be generated rapidly, under mild conditions and by means of a linking moiety that remains more stable to storage and administration of the complex.

SUMMARY OF THE INVENTION

In a first aspect, the present invention therefore provides a method for the formation of a tissue-targeting thorium complex, said method comprising:

a) forming an octadentate chelator of formula (I) or (II):

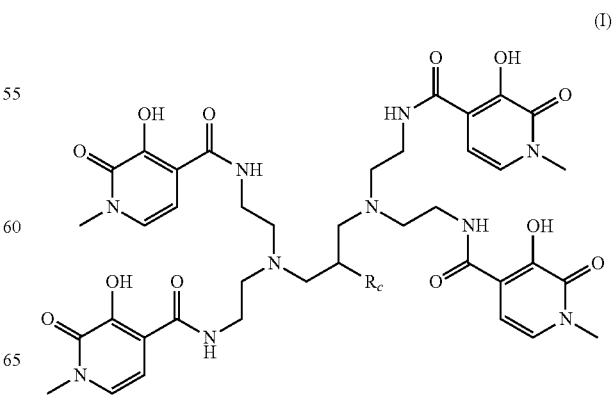

(II)

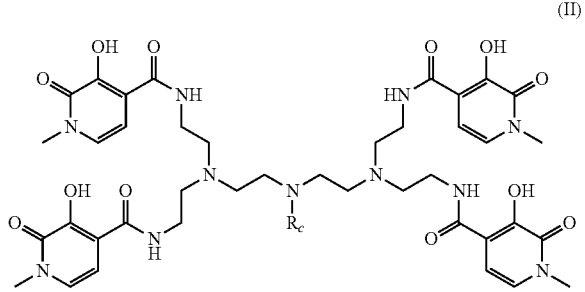

wherein $R_c$ is a linker moiety terminating in a carboxylic acid moiety, such as
[—CH$_2$—Ph—N(H)—C(=O)—CH$_2$—CH$_2$—C(=O)OH],
[—CH$_2$—CH$_2$—N(H)—C(=O)—(CH$_2$—CH$_2$—O)$_{1-3}$—CH$_2$—CH$_2$—C(=O)OH] or
[—(CH$_2$)$_{1-3}$-Ph-N(H)—C(=O)—(CH$_2$)$_{1-5}$—C(=O)OH], wherein Ph is a phenylene group, preferably a para-phenylene group;

b) coupling said octadentate chelator to a tissue-targeting moiety comprising a peptide chain with sequence identity with the sequence 1:

Light Chain
(SEQ ID NO. 1)
DIQMTQSPSSLSASVGDRVTITCRASQDVNTAVAWYQQKPGKAPKWYSAS

FLYSGVPSRFSGSRSGTDFTLTISSLQPEDFATYYCQQHYTTPPTFGQGT

KVEIKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLS

SPVTKSFNRGEC and a peptide chain with sequence similarity or identity with any one of the following sequences 2 to 6:

Heavy Chain
(SEQ ID NO. 2)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG (SEQ ID NO. 3)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG (SEQ ID NO. 4)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYA

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG (SEQ ID NO. 5)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYQ

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG (SEQ ID NO. 6)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREENYQ

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG thereby generating a tissue-targeting chelator; and c) contacting said tissue-targeting chelator with an aqueous solution comprising 4+ ions of the alpha-emitting thorium isotope $^{227}$Th.

In such complexes (and preferably in all aspects of the current invention) the thorium ion will generally be complexed by the octadentate hydroxypyridinone-containing ligand, which in turn will be attached to the tissue targeting moiety via an amide bond.

Typically, the method will be a method for the synthesis of 3,2-hydroxypyridinone-based octadentate chelates comprising a reactive carboxylate function which can be activated in the form of an active ester (such as an N-hydroxysuccinimide ester (NHS ester)) either via in situ activation or by synthesis and isolation of the active ester itself.

The resulting NHS ester can be used in a simple conjugation step to produce a wide range of chelate modified protein formats. In addition, highly stable antibody conjugates are readily labelled with thorium-227. This may be at or close to ambient temperature, typically in high radiochemical yields and purity.

The method of the invention will preferably be carried out in aqueous solution and in one embodiment may be carried out in the absence or substantial absence (less than 1% by volume) of any organic solvent.

The tissue targeting complexes of the present invention may be formulated into medicaments suitable for administration to a human or non-human animal subject.

In a second aspect the invention therefore provides methods for the generation of a pharmaceutical formulation comprising forming a tissue-targeting complex as described herein followed by addition of at least one pharmaceutical carrier and/or excipient. Suitable carriers and excipients include buffers, chelating agents, stabilising agents and other suitable components known in the art and described in any aspect herein.

In a further aspect, the invention additionally provides a tissue-targeting thorium complex. Such a complex will have the features described herein throughout, particularly the preferred features described herein. The complex may be formed or formable by any of the methods described herein. Such methods may thus yield at least one tissue-targeting thorium complex as described in any aspect or embodiment herein.

In a still further aspect, the present invention provides a pharmaceutical formulation comprising any of the complexes described herein. The formulation may be formed or formable by any of the methods described herein and may contain at least one buffer, stabiliser and/or excipient. The choice of buffer and stabiliser may be such that together they help to protect the tissue-targeting complex from radiolysis. In one embodiment, radiolysis of the complex in the formulation is minimal even after several days post manufacture of the formulation. This is an important advantage because it solves potential issues associated with product quality and the logistics of drug supply which are key to enablement and practical application of this technology.

DETAILED DESCRIPTION OF THE INVENTION

In the context of the present invention, "tissue targeting" is used herein to indicate that the substance in question (particularly when in the form of a tissue-targeting complex as described herein), serves to localise itself (and particularly to localise any conjugated thorium complex) preferentially to at least one tissue site at which its presence (e.g. to deliver a radioactive decay) is desired. Thus a tissue targeting group or moiety serves to provide greater localisation to at least one desired site in the body of a subject following administration to that subject in comparison with the concentration of an equivalent complex not having the targeting moiety.

The targeting moiety in the present case has specificity for HER2.

The various aspects of the invention as described herein relate to treatment of disease, particularly for the selective targeting of diseased tissue, as well as relating to complexes, conjugates, medicaments, formulation, kits etc. useful in such methods. In all aspects, the diseased tissue may reside at a single site in the body (for example in the case of a localised solid tumour) or may reside at a plurality of sites (for example where several joints are affected in arthritis or in the case of a distributed or metastasised cancerous disease).

The diseased tissue to be targeted may be at a soft tissue site, at a calcified tissue site or a plurality of sites which may all be in soft tissue, all in calcified tissue or may include at least one soft tissue site and/or at least one calcified tissue site. In one embodiment, at least one soft tissue site is targeted. The sites of targeting and the sites of origin of the disease may be the same, but alternatively may be different (such as where metastatic sites are specifically targeted). Where more than one site is involved this may include the site of origin or may be a plurality of secondary sites.

The term "soft tissue" is used herein to indicate tissues which do not have a "hard" mineralised matrix. In particular, soft tissues as used herein may be any tissues that are not skeletal tissues. Correspondingly, "soft tissue disease" as used herein indicates a disease occurring in a "soft tissue" as used herein. The invention is particularly suitable for the treatment of cancers and "soft tissue disease" thus encompasses carcinomas, sarcomas, myelomas, leukemias, lymphomas and mixed type cancers occurring in any "soft" (i.e. non-mineralised) tissue, as well as other non-cancerous diseases of such tissue. Cancerous "soft tissue disease" includes solid tumours occurring in soft tissues as well as metastatic and micro-metastatic tumours. Indeed, the soft tissue disease may comprise a primary solid tumour of soft tissue and at least one metastatic tumour of soft tissue in the same patient. Alternatively, the "soft tissue disease" may consist of only a primary tumour or only metastases with the primary tumour being a skeletal disease.

Examples of neoplasms suitable for treatment using a Human Epidermal Growth Factor Receptor-2 (HER2) targeted agent of the present invention include breast cancers, gastric cancers, ovarian cancers, non-small-cell lung carcinomas (NSCLC), and uterine cancers.

It is a key contribution to the success of this invention that the antibody conjugates are stable for acceptable periods of time on storage. Hence the stability of both the non-radioactive antibody conjugate and the final thorium-labelled drug product must meet the stringent criteria demanded for manufacture and distribution of radiopharmaceutical products. It was a surprising finding that the formulation described herein comprising a tissue-targeting complex demonstrates outstanding stability on storage. This applies even at the elevated temperatures typically used for accelerated stability studies.

In one embodiment applicable to all compatible aspects of the invention, the tissue-targeting complex may be dissolved in a suitable buffer. In particular, it has been found that the use of a citrate buffer provides a surprisingly stable formulation. This is preferably citrate buffer in the range 1-100 mM (pH 4-7), particularly in the range 10 to 50 mM, but most preferably 20-40 mM citrate buffer.

In a further embodiment applicable to all compatible aspects of the invention, the tissue-targeting complex may be dissolved in a suitable buffer containing p-aminobutyric acid (PABA). A preferred combination is citrate buffer (preferably at the concentrations described herein) in combination with PABA. Preferred concentrations for PABA for use in any aspect of the present invention, including in combination with other agents is around 0.005 to 5 mg/ml, preferably 0.01 to 1 mg/ml and more preferably 0.01 to 1 mg/ml. Concentrations of 0.1 to 0.5 mg/ml are most preferred.

In a further embodiment applicable to all compatible aspects of the invention, the tissue-targeting complex may be dissolved in a suitable buffer containing ethylenediaminetetraacetic acid (EDTA). A preferred combination is the use of EDTA with citrate buffer. A particularly preferred combination is the use of EDTA with citrate buffer in the presence of PABA. It is preferred in such combinations that citrate, PABA and EDTA as appropriate will be present in the ranges of concentration and preferred ranges of concentration indicated herein. Preferred concentrations for EDTA for use in any aspect of the present invention, including in combination with other agents is around 0.02 to 200 mM, preferably 0.2 to 20 mM and most preferably 0.05 to 8 mM.

In a further embodiment applicable to all compatible aspects of the invention, the tissue-targeting complex may be dissolved in a suitable buffer containing at least one polysorbate (PEG grafted sorbitan fatty-acid ester). Preferred polysorbates include Polysorbate 80 (Polyoxyethylene (20) sorbitan monooleate), Polysorbate 60 (Polyoxyethylene (20) sorbitan monostearate), Polysorbate 40 (Polyoxyethylene (20) sorbitan monopalmitate), Polysorbate 80 (Polyoxyethylene (20) sorbitan monolaurate) and mixtures thereof. Polysorbate 80 (P80) is a most preferred polysorbate. Preferred concentrations for polysorbate (especially preferred polysorbates as indicated herein) for use in any aspect of the present invention, including in combination with other agents is around 0.001 to 10% w/v, preferably 0.01 to 1% w/v and most preferably 0.02 to 0.5 w/v.

Although PABA has been previously described as a radiostabilizer (see U.S. Pat. No. 4,880,615 A) a positive effect of PABA in the present invention was observed on the non-radioactive conjugate on storage. This stabilising effect in the absence of radiolysis constitutes a particularly surprising advantage because the synthesis of the tissue-targeting chelator will typically take place significantly before contacting with the thorium ion. Thus, the tissue-targeting chelator may be generated 1 hour to 3 years prior to contact with the thorium ion and will preferably be stored in contact with PABA during at least a part of that period. That is to say, steps a) and b) of the present invention may take place 1 hour to 3 years before step c) and between steps b) and c), the tissue-targeting chelator may be stored in contact with PABA, particularly in a buffer, such as a citrate buffer and optionally with EDTA and/or a polysorbate. All materials preferably being the type and concentrations indicated herein. PABA is thus a highly preferred component of the formulations of the invention and can result in long term stability for the tissue-targeting chelator and/or for the tissue-targeting thorium complex.

The use of citrate buffer as described herein provides a further surprising advantage with regard to the stability of the tissue-targeting thorium complex in the formulations of the present invention. An irradiation study on the effect of buffer-solutions on hydrogen peroxide generation was carried out by the present inventors with unexpected results.

Hydrogen peroxide is known to form as a result of water radiolysis and contributes to chemical modification of protein conjugates in solution. Hydrogen peroxide generation therefore has an undesirable effect on the purity and stability of the product. FIG. 2 shows the surprising observation that lower levels of hydrogen peroxide were measured in the antibody HOPO conjugate solutions of this invention irradiated with Co-60 (10 kGy) in citrate buffer compared to all other buffers tested. Thus, the formulations of the present invention will preferably comprising citrate buffer as described herein.

The present inventors have additionally established a further surprising finding relating to the combined effect of certain components in the formulations of this invention. This relates again to the stability of the radiolabelled conjugate. Citrate having been found to be the most effective buffer, it was surprising to find that this effect was improved still further by the addition of PABA.

A key component of the methods, complexes and formulations of the present invention is the octadentate chelator moiety. The most relevant previous work on complexation of thorium ions with hydroxypyridinone ligands was published as WO2011/098611 and discloses the relative ease of generation of thorium ions complexed with octadentate HOPO-containing ligands.

Previously known chelators for thorium also include the polyaminopolyacid chelators which comprise a linear, cyclic or branched polyazaalkane backbone with acidic (e.g. carboxyalkyl) groups attached at backbone nitrogens. Examples of such chelators include DOTA derivatives such as p-isothiocyanatobenzyl-1,4,7,10-tetraazacyclododecane-1,4,7,10-tetraacetic acid (p-SCN-Bz-DOTA) and DTPA derivatives such as p-isothiocyanatobenzyl-diethylenetriaminepentaacetic acid (p-SCN-Bz-DTPA), the first being cyclic chelators, the latter linear chelators.

Derivatives of 1,4,7,10-tetraazacyclododecane-1,4,7,10-tetraacetic acid have been previously exemplified, but standard methods cannot easily be used to chelate thorium with DOTA derivatives. Heating of the DOTA derivative with the metal provides the chelate effectively, but often in low yields. There is a tendency for at least a portion of the ligand to irreversibly denature during the procedure. Furthermore, because of its relatively high susceptibility to irreversible denaturation, it is generally necessary to avoid attachment of the targeting moiety until all heating steps are completed. This adds an extra chemical step (with all necessary work-up and separation) which must be carried out during the decay lifetime of the alpha-emitting thorium isotope. Obviously it is preferable not to handle alpha-emitting material in this way or to generate corresponding waste to a greater extent than necessary. Furthermore, all time spent preparing the conjugate wastes a proportion of the thorium which will decay during this preparatory period.

A key aspect of the present invention in all respects is the use of an octadentate chelator of formula (I) or (II):

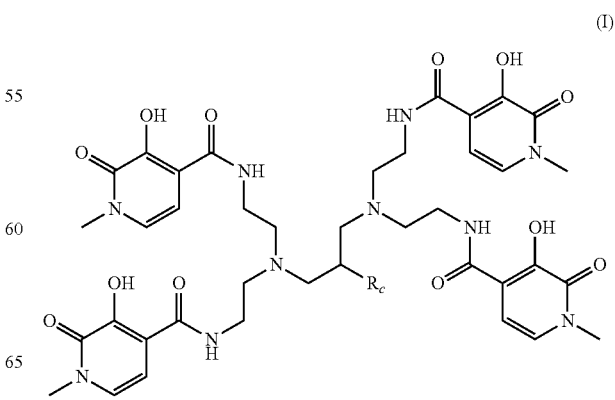

(I)

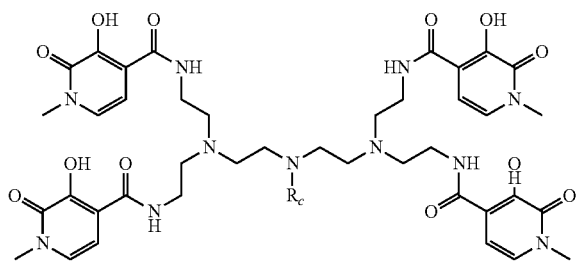

(II)

wherein Rc is a linker moiety terminating in a carboxylic acid moiety, such as

[—CH$_2$-Ph-N(H)—C(=O)—CH$_2$—CH$_2$—C(=O)OH],

[—CH$_2$—CH$_2$—N(H)—C(=O)—(CH$_2$—CH$_2$—O)$_{1-3}$—CH$_2$—CH$_2$—C(=O)OH] or

[—(CH$_2$)$_{1-3}$-Ph-N(H)—C(=O)—(CH$_2$)$_{1-5}$—C(=O)OH], wherein Ph is a phenylene group, preferably a para-phenylene group.

In certain previous disclosures, such as WO2013/167756, WO2013/167755 and WO2013/167754 the methyl group attached to the N-atom of the 3,2-HOPO moiety has primarily been a solubilising group such as hydroxy or hydroxyalkyl (e.g. —CH$_2$OH, —CH$_2$—CH$_2$OH, —CH$_2$—CH$_2$—CH$_2$OH etc.). This has certain advantages in terms of higher solubility, but such chelators are difficult to join to targeting moieties using amide bonds.

The chelating moieties may be formed by methods known in the art, including the methods described in U.S. Pat. No. 5,624,901 (e.g. examples 1 and 2) and WO2008/063721 (both incorporated herein by reference).

R$_C$ represents a coupling moiety. Suitable moieties include hydrocarbyl groups such as alkyl or akenyl groups terminating in a carboxylic acid group. It has been established by the present inventors that use of a carboxylic acid linking moiety to form an amide, such as by the methods of the present invention, provides a more stable conjugation between the chelator and the tissue-targeting moiety.

In the most preferred embodiment of this invention the coupling moiety (R$_c$) linking the octadentate ligand to the targeting moiety is chosen to be

[—CH$_2$-Ph-N(H)—C(=O)—CH$_2$—CH$_2$—C(=O)OH],

[—CH$_2$—CH$_2$—N(H)—C(=O)—(CH$_2$—CH$_2$—O)$_{1-3}$—CH$_2$—CH$_2$—C(=O)OH] or

[—(CH$_2$)$_{1-3}$-Ph-N(H)—C(=O)—(CH$_2$)$_{1-5}$—C(=O)OH], wherein Ph is a phenylene group, preferably a para-phenylene group.

In a preferred embodiment, R$_c$ is [—(CH$_2$)$_{1-3}$-Ph-N(H)—C(=O)—(CH$_2$)$_{1-5}$—C(=O)OH]. In a more preferred embodiment, R$_c$ is [—(CH$_2$)-para-phenylene-N(H)—C(=O)—(CH$_2$)$_2$—C(=O)OH].

Highly preferred octadentate chelators include those of formulae (III) and (IV) below:

(III)

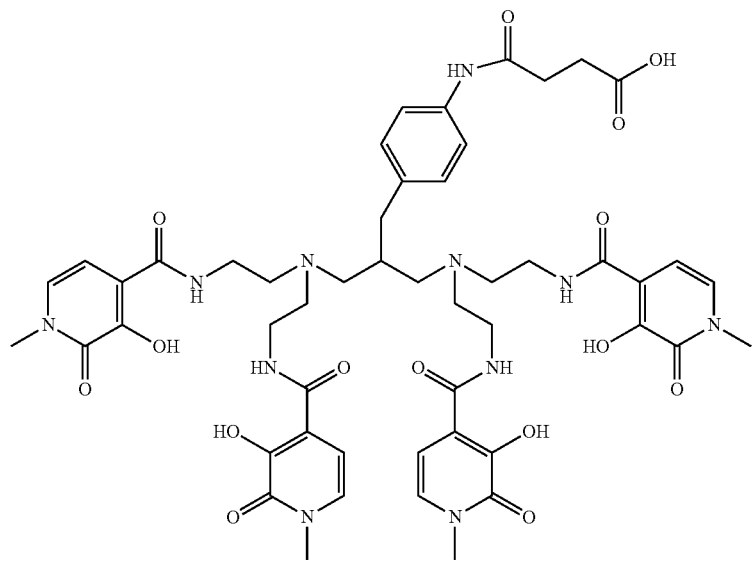

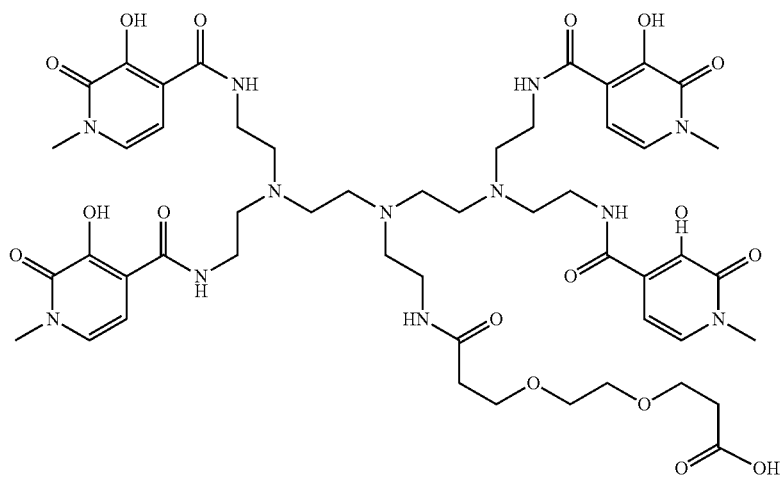

(IV)

The synthesis of compound (III) is described herein below and follows the synthetic route described herein below.

Step a) of the methods of the present invention may be carried out by any suitable synthetic route. Some specific examples of synthetic methods are given below in the following Examples. Such methods provide specific examples, but the synthetic methods illustrated therein will also be usable in a general context by those of skill in the art. The methods illustrated in the Examples are therefore intended also as general disclosures applicable to all aspects and embodiments of the invention where context allows.

It is preferred that the complexes of alpha-emitting thorium and an octadentate ligand in all aspects of the present invention are formed or formable without heating above 60° C. (e.g. without heating above 50° C.), preferably without heating above 38° C. and most preferably without heating above 25° C. (such as in the range 20 to 38° C.). Typical ranges may be, for example 15 to 50° C. or 20 to 40° C. The complexation reaction (part c)) in the methods of the present invention) may be carried out for any reasonable period but this will preferably be between 1 and 120 minutes, preferably between 1 and 60 minutes, and more preferably between 5 and 30 minutes.

It is additionally preferred that the conjugate of the targeting moiety and the octadentate ligand be prepared prior to addition of the alpha-emitting thorium isotope $^{227}$Th$^{4+}$ ion. The products of the invention are thus preferably formed or formable by complexation of alpha-emitting thorium isotope ($^{227}$Th$^{4+}$ ion) by a conjugate of an octadentate ligand and a tissue-targeting moiety (the tissue-targeting chelator).

Various types of targeting compounds may be linked to thorium (e.g. thorium-227) via an octadentate chelator (comprising a coupling moiety as described herein).

Generally, as used herein, the tissue targeting moieties will be "peptides" or "proteins", being structures formed primarily of an amide backbone between amino-acid components either with or without secondary and tertiary structural features.

According to this invention $^{227}$Th may be complexed by targeting complexing agents joined or joinable by an amide linkage to tissue-targeting moieties as described herein.

Typically the targeting moieties will have a molecular weight from 100 g/mol to several million g/mol (particularly 100 g/mol to 1 million g/mol), and will preferably have affinity for a disease-related receptor either directly, and/or will comprise a suitable pre-administered binder (e.g. biotin or avidin) bound to a molecule that has been targeted to the disease in advance of administering $^{227}$Th.

The specific binder (tissue targeting moiety) of the present invention is chosen to target the HER2 antigen.

The tissue targeting moiety of the present invention comprises a peptide chain with sequence identity with the sequence 1:

Light Chain
(SEQ ID NO. 1)
DIQMTQSPSSLSASVGDRVTITCRASQDVNTAVAWYQQKPGKAPKWYSAS

FLYSGVPSRFSGSRSGTDFTLTISSLQPEDFATYYCQQHYTTPPTFGQGT

KVEIKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLS

SPVTKSFNRGEC and a peptide chain with sequence similarity or identity with any one of the following sequences 2 to 6:

Heavy Chain
(SEQ ID NO. 2)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG (SEQ ID NO. 3)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

-continued
GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG (SEQ ID NO. 4)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYA

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG (SEQ ID NO. 5)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYQ

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG (SEQ ID NO. 6)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREENYQ

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

In a preferred embodiment, the tissue-targeting moiety comprises a peptide chain with sequence identity with the sequence 1:

Light Chain
(SEQ ID NO. 1)
DIQMTQSPSSLSASVGDRVTITCRASQDVNTAVAWYQQKPGKAPKWYSAS

FLYSGVPSRFSGSRSGTDFTLTISSLQPEDFATYYCQQHYTTPPTFGQGT

KVEIKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLS

SPVTKSFNRGEC and a peptide chain with sequence similarity or identity with sequence 2:

Heavy Chain
(SEQ ID NO. 2)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPG.

Substantial sequence identity/similarity may be taken as having a sequence similarity/identity of at least 80% to the complete sequences and/or at least 90% to the specific binding regions (those regions shown in bold in the above sequences and optionally those sections underlined). Preferable sequence similarity or more preferably identity may be at least 92%, 95%, 97%, 98% or 99% for the bold regions and preferably also for the full sequences. Sequence similarity and/or identity may be determined using the "BestFit" program of the Genetics Computer Group Version 10 software package from the University of Wisconsin. The program uses the local had algorithm of Smith and Waterman with default values: Gap creation penalty=8, Gap extension penalty=2, Average match=2.912, average mismatch 2.003.

In a preferred embodiment, the tissue-targeting moiety comprises a peptide chain with sequence identity with the sequence 1, and a peptide chain with sequence similarity of 98% or more or identity with any one of the sequences 2 to 6.

In a more preferred embodiment, the tissue-targeting moiety comprises a peptide chain with sequence identity with the sequence 1, and a peptide chain with sequence similarity of 99% or more or identity with any one of the sequences 2 to 6.

In another preferred embodiment, the tissue-targeting moiety comprises a peptide chain with sequence identity with the sequence 1, and a peptide chain with sequence similarity of 98% or more or identity with the sequence 2.

In a more preferred embodiment, the tissue-targeting moiety comprises a peptide chain with sequence identity with the sequence 1, and a peptide chain with sequence similarity of 99% or more or identity with the sequence 2.

The tissue targeting moiety of the present invention represents variants of trastuzumab:

SEQ ID NOs. 1 and 2: trastuzumab without C-terminal lysine

SEQ ID NOs. 1 and 3: trastuzumab without C-terminal lysine and heavy chain mutations E359D, M361L SEQ ID NOs. 1 and 4: trastuzumab without C-terminal lysine and heavy chain mutations N300A, E359D, M361L SEQ ID NOs. 1 and 5: trastuzumab without C-terminal lysine and heavy chain mutations N300Q, E359D, M361L SEQ ID NOs. 1 and 6: trastuzumab without C-terminal lysine and heavy chain mutations Q298N, N300Q E359D, M361 L The antibody to HER2 of the present invention can be prepared by recombinant expression of nucleic acid sequences encoding light and heavy chains or portions thereof in a host cell. To express an antibody, antigen binding portion, or variant thereof recombinantly a host cell can be transfected with one or more recombinant expression vectors carrying DNA fragments encoding the light and/or heavy chains or portions thereof such that the light and heavy chains are expressed in the host cell. Standard recombinant DNA methodologies are used to prepare and/or obtain nucleic acids encoding the heavy and light chains, incorporate these nucleic acids into recombinant expression vectors and introduce the vectors into host cells, such as those described in Sambrook, Fritsch and Maniatis (eds.), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397 by Boss et al.

In addition, the nucleic acid sequences encoding variable regions of the heavy and/or light chains can be converted, for example, to nucleic acid sequences encoding full-length antibody chains, Fab fragments, or to scFv. The VL- or VH-encoding DNA fragment can be operatively linked, (such that the amino acid sequences encoded by the two DNA fragments are in-frame) to another DNA fragment encoding, for example, an antibody constant region or a flexible linker. The sequences of human heavy chain and light chain constant regions are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification.

To create a polynucleotide sequence that encodes a scFv, the VH- and VL-encoding nucleic acids can be operatively linked to another fragment encoding a flexible linker such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., Nature (1990) 348:552-554).

To express the antibodies, antigen binding fragments thereof or variants thereof standard recombinant DNA expression methods can be used (see, for example, Goeddel; Gene Expression Technology. Methods in Enzymology 185, Academic Press, San Diego, Calif. (1990)). For example, DNA encoding the desired polypeptide can be inserted into an expression vector which is then transfected into a suitable host cell. Suitable host cells are prokaryotic and eukaryotic cells. Examples for prokaryotic host cells are e.g. bacteria, examples for eukaryotic hosts cells are yeasts, insects and insect cells, plants and plant cells, transgenic animals, or mammalian cells. In some embodiments, the DNAs encoding the heavy and light chains are inserted into separate vectors. In other embodiments, the DNA encoding the heavy and light chains is inserted into the same vector. It is understood that the design of the expression vector, including the selection of regulatory sequences is affected by factors such as the choice of the host cell, the level of expression of protein desired and whether expression is constitutive or inducible.

Useful expression vectors for bacterial use are constructed by inserting a DNA sequence encoding a desired protein together with suitable translation initiation and termination signals in operable reading phase with a functional promoter. The vector will comprise one or more phenotypic selectable markers and an origin of replication to ensure maintenance of the vector and, if desirable, to provide amplification within the host. Suitable prokaryotic hosts for transformation include but are not limited to *E. coli, Bacillus subtilis, Salmonella typhimurium* and various species within the genera *Pseudomonas, Streptomyces*, and *Staphylococcus*.

Bacterial vectors may be, for example, bacteriophage-, plasmid- or phagemid-based. These vectors can contain a selectable marker and a bacterial origin of replication derived from commercially available plasmids typically containing elements of the well-known cloning vector pBR322 (ATCC 37017). Following transformation of a suitable host strain and growth of the host strain to an appropriate cell density, the selected promoter is de-repressed/induced by appropriate means (e.g., temperature shift or chemical induction) and cells are cultured for an additional period. Cells are typically harvested by centrifugation, disrupted by physical or chemical means, and the resulting crude extract retained for further purification.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable.

Antibodies of the present invention or antigen-binding fragments thereof or variants thereof include naturally purified products, products of chemical synthetic procedures, and products produced by recombinant techniques from a prokaryotic host, including, for example, *E. coli, Bacillus subtilis, Salmonella typhimurium* and various species within the genera *Pseudomonas, Streptomyces, and Staphylococcus*, preferably, from *E. coli* cells.

Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. Expression of the antibodies may be constitutive or regulated (e.g. inducible by addition or removal of small molecule inductors such as Tetracyclin in conjunction with Tet system). For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al. The recombinant expression vectors can also include origins of replication and selectable markers (see e.g., U.S. Pat. Nos. 4,399,216, 4,634,665 and 5,179,017). Suitable selectable markers include genes that confer resistance to drugs such as G418, puromycin, hygromycin, blasticidin, zeocin/bleomycin or methotrexate or selectable marker that exploit auxotrophies such as Glutamine Synthetase (Bebbington et al., Biotechnology (N Y). 1992 February; 10(2):169-75), on a host cell into which the vector has been introduced. For example, the dihydrofolate reductase (DHFR) gene confers resistance to methotrexate, neo gene confers resistance to G418, the bsd gene from *Aspergillus terreus* confers resistance to blasticidin, puromycin N-acetyl-transferase confers resistance to puromycin, the Sh ble gene product confers resitance to zeocin, and resistance to hygromycin is conferred by the *E. coli* hygromycin resistance gene (hyg or hph). Selectable markers like DHFR or Glutamine Synthetase are also useful for amplification techniques in conjunction with MTX and MSX.

Transfection of the expression vector into a host cell can be carried out using standard techniques such as electroporation, nucleofection, calcium-phosphate precipitation, lipofection, polycation-based transfection such as polyethylenimine (PEI)-based transfection and DEAE-dextran transfection.

Suitable mammalian host cells for expressing the antibodies, antigen binding fragments thereof or variants thereof provided herein include but are not limited to Chinese Hamster Ovary (CHO cells) such as CHO-K1, CHO-S, CHO-K1SV [including dhfr-CHO cells, described in Urlaub and Chasin, (1980) Proc. Natl. Acad. Sci. USA 77:4216-4220 and Urlaub et al., Cell. 1983 June; 33(2):405-12, used with a DHFR selectable marker, e.g., as described in R. J. Kaufman and P. A. Sharp (1982) Mol. Biol. 159:601-621; and other knockout cells exemplified in Fan et al., Biotechnol Bioeng. 2012 April; 109(4):1007-15], NS0 myeloma cells, COS cells, HEK293 cells, HKB11 cells, BHK21 cells, CAP cells, EB66 cells, and SP2 cells. Expression might also be transient or semi-stable in expression systems such as HEK293, HEK293T, HEK293-EBNA, HEK293E, HEK293-6E, HEK293-Freestyle, HKB11, Expi293F, 293EBNALT75, CHO Freestyle, CHO-S, CHO-K1, CHO-K1SV, CHOEBNALT85, CHOS-XE, CHO-3E7 or CAP-T cells (for instance Durocher et al., Nucleic Acids Res. 2002 Jan. 15; 30(2):E9).

In some embodiments, the expression vector is designed such that the expressed protein is secreted into the culture medium in which the host cells are grown. The antibodies, antigen binding fragments thereof or variants thereof can be recovered from the culture medium using standard protein purification methods.

Antibodies of the invention or antigen-binding fragments thereof or variants thereof can be recovered and purified from recombinant cell cultures by well-known methods including, but not limited to ammonium sulfate or ethanol precipitation, acid extraction, Protein A chromatography, Protein G chromatography, anion or cation exchange chromatography, phospho-cellulose chromatography, hydrophobic interaction chromatography, affinity chromatography, hydroxylapatite chromatography, mixed mode chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention or antigen-binding fragments thereof or variants thereof include naturally purified products, products of chemical synthetic procedures, and products produced by recombinant techniques from an eukaryotic host, including, for example, yeast, higher plant, insect and mammalian cells. Depending upon the host employed in a recombinant production procedure, the antibody of the present invention can be glycosylated or can be non-glycosylated. Such methods are described in many standard laboratory manuals, such as Sambrook, supra, Sections 17.37-17.42; Ausubel, supra, Chapters 10, 12, 13, 16, 18 and 20.

In preferred embodiments, the antibody is purified (1) to greater than 95% by weight of antibody as determined e.g. by the Lowry method, UV-Vis spectroscopy or by by SDS-Capillary Gel electrophoresis (for example on a Caliper LabChip GXII, GX 90 or Biorad Bioanalyzer device), and in further preferred embodiments more than 99% by weight, (2) to a degree sufficient to obtain at least 15 residues of N-terminal or internal amino acid sequence, or (3) to homogeneity by SDS-PAGE under reducing or non-reducing conditions using Coomassie blue or, preferably, silver stain. Isolated naturally occurring antibody includes the antibody in situ within recombinant cells since at least one component of the antibody's natural environment will not be present. Ordinarily, however, isolated antibody will be prepared by at least one purification step.

With regard to the alpha-emitting thorium component, it is a key recent finding that $^{227}$Th may be administered in an amount that is both therapeutically effective and does not generate intolerable myelotoxicity. As used herein, the term "acceptably non-myelotoxic" is used to indicate that, most importantly, the amount of radium-223 generated by decay of the administered thorium-227 radioisotope is generally not sufficient to be directly lethal to the subject. It will be clear to the skilled worker, however, that the amount of marrow damage (and the probability of a lethal reaction) which will be an acceptable side-effect of such treatment will vary significantly with the type of disease being treated, the goals of the treatment regimen, and the prognosis for the subject. Although the preferred subjects for the present invention are humans, other mammals, particularly companion animals such as dogs, will benefit from the use of the invention and the level of acceptable marrow damage may also reflect the species of the subject. The level of marrow damage acceptable will generally be greater in the treatment of malignant disease than for non-malignant disease. One well known measure of the level of myelotoxicity is the neutrophil cell count and, in the present invention, an acceptably non-myelotoxic amount of $^{223}$Ra will typically be an amount controlled such that the neutrophil fraction at its lowest point (nadir) is no less than 10% of the count prior to treatment. Preferably, the acceptably non-myelotoxic amount of $^{223}$Ra will be an amount such that the neutrophil cell fraction is at least 20% at nadir and more preferably at least 30%. A nadir neutrophil cell fraction of at least 40% is most preferred.

In addition, radioactive $^{227}$Th containing compounds may be used in high dose regimens where the myelotoxicity of the generated $^{223}$Ra would normally be intolerable when stem cell support or a comparable recovery method is included. In such cases, the neutrophil cell count may be reduced to below 10% at nadir and exceptionally will be reduced to 5% or if necessary below 5%, providing suitable precautions are taken and subsequent stem cell support is given. Such techniques are well known in the art.

Thorium-227 is relatively easy to produce and can be prepared indirectly from neutron irradiated 226Ra, which will contain the mother nuclide of $^{227}$Th, i.e. $^{227}$Ac ($T_{1/2}$=22 years). Actinium-227 can quite easily be separated from the $^{226}$Ra target and used as a generator for $^{227}$Th. This process can be scaled to industrial scale if necessary, and hence the supply problem seen with most other alpha-emitters considered candidates for molecular targeted radiotherapy can be avoided.

Thorium-227 may be administered in amounts sufficient to provide desirable therapeutic effects without generating so much radium-223 as to cause intolerable bone marrow suppression. It is desirable to maintain the daughter isotopes in the targeted region so that further therapeutic effects may be derived from their decay. However, it is not necessary to maintain control of the thorium decay products in order to have a useful therapeutic effect without inducing unacceptable myelotoxicity.

Assuming the tumour cell killing effect will be mainly from thorium-227 and not from its daughters, the likely therapeutic dose of this isotope can be established by comparison with other alpha emitters. For example, for astatine-211, therapeutic doses in animals have been typically 2-10 MBq per kg. By correcting for half-life and energy the corresponding dosage for thorium-227 would be at least 36-200 kBq per kg of bodyweight. This would set a lower limit on the amount of $^{227}$Th that could usefully be administered in expectation of a therapeutic effect. This calculation assumes comparable retention of astatine and thorium. Clearly however the 18.7 day half-life of the thorium will most likely result in greater elimination of this isotope before its decay. This calculated dosage should therefore normally be considered to be the minimum effective amount. The therapeutic dose expressed in terms of fully retained $^{227}$Th (i.e. $^{227}$Th which is not eliminated from the body) will typically be at least 18 or 25 kBq/kg, preferably at least 36 kBq/kg and more preferably at least 75 kBq/kg, for example 100 kBq/kg or more. Greater amounts of thorium would be expected to have greater therapeutic effect but cannot be administered if intolerable side effects will result. Equally, if the thorium is administered in a form having a short biological half-life (i.e. the half life before elimination from the body still carrying the thorium), then greater amounts of the radioisotope will be required for a therapeutic effect because much of the thorium will be eliminated before it decays. There will, however, be a corresponding decrease in the amount of radium-223 generated. The above amounts of thorium-227 to be administered when the isotope is fully retained may easily be related to equivalent doses with shorter biological half-lives. Such calculations are well known in the art and given in WO 04/091668 (e.g. in the text an in Examples 1 and 2).

If a radiolabelled compound releases daughter nuclides, it is important to know the fate, if applicable, of any radioactive daughter nuclide(s). With $^{227}$Th, the main daughter product is $^{223}$Ra, which is under clinical evaluation because of its bone seeking properties. Radium-223 clears blood very rapidly and is either concentrated in the skeleton or excreted via intestinal and renal routes (see Larsen, J Nucl Med 43(5, Supplement): 160P (2002)). Radium-223 released in vivo from $^{227}$Th may therefore not affect healthy soft tissue to a great extent. In the study by Müller in Int. J. Radiat. Biol. 20:233-243 (1971) on the distribution of $^{227}$Th as the dissolved citrate salt, it was found that $^{223}$Ra generated from $^{227}$Th in soft tissues was readily redistributed to bone or was excreted. The known toxicity of alpha emitting radium, particularly to the bone marrow, is thus an issue with thorium dosages.

It was established for the first time in WO 04/091668 that, in fact, a dose of at least 200 kBq/kg of $^{223}$Ra can be administered and tolerated in human subjects. These data are presented in that publication. Therefore, it can now be seen that, quite unexpectedly, a therapeutic window does exist in which a therapeutically effective amount of $^{227}$Th (such as greater than 36 kBq/kg) can be administered to a mammalian subject without the expectation that such a subject will suffer an unacceptable risk of serious or even lethal myelotoxicity. Nonetheless, it is extremely important that the best use of this therapeutic window be made and therefore it is essential that the radioactive thorium be quickly and efficiently complexed, and held with very high affinity so that the greatest possible proportion of the dose is delivered to the target site.

The amount of $^{223}$Ra generated from a $^{227}$Th pharmaceutical will depend on the biological half-life of the radiolabelled compound. The ideal situation would be to use a complex with a rapid tumour uptake, including internalization into tumour cell, strong tumour retention and a short biological half-life in normal tissues. Complexes with less than ideal biological half-life can however be useful as long as the dose of $^{223}$Ra is maintained within the tolerable level. The amount of radium-223 generated in vivo will be a factor of the amount of thorium administered and the biological retention time of the thorium complex. The amount of radium-223 generated in any particular case can be easily calculated by one of ordinary skill. The maximum administrable amount of $^{227}$Th will be determined by the amount of radium generated in vivo and must be less than the amount that will produce an intolerable level of side effects, particularly myelotoxicity. This amount will generally be less than 300 kBq/kg, particularly less than 200 kBq/kg and more preferably less than 170 kBq/kg (e.g. less than 130 kBq/kg). The minimum effective dose will be determined by the cytotoxicity of the thorium, the susceptibility of the diseased tissue to generated alpha irradiation and the degree to which the thorium is efficiently combined, held and delivered by the targeting complex (being the combination of the ligand and the targeting moiety in this case).

In the method of invention, the thorium complex is desirably administered at a thorium-227 dosage of 18 to 400 kBq/kg bodyweight, preferably 36 to 200 kBq/kg, (such as 50 to 200 kBq/kg) more preferably 75 to 170 kBq/kg, especially 100 to 130 kBq/kg. Correspondingly, a single dosage until may comprise around any of these ranges multiplied by a suitable bodyweight, such as 30 to 150 Kg, preferably 40 to 100 Kg (e.g. a range of 540 kBq to 4000 KBq per dose etc.). The thorium dosage, the complexing agent and the administration route will moreover desirably be such that the radium-223 dosage generated in vivo is less than 300 kBq/kg, more preferably less than 200 kBq/kg, still more preferably less than 150 kBq/kg, especially less than 100 kBq/kg. Again, this will provide an exposure to $^{223}$Ra indicated by multiplying these ranges by any of the bodyweights indicated. The above dose levels are preferably the fully retained dose of $^{227}$Th but may be the administered dose taking into account that some $^{227}$Th will be cleared from the body before it decays.

Where the biological half-life of the $^{227}$Th complex is short compared to the physical half-life (e.g. less than 7 days, especially less than 3 days) significantly larger administered doses may be needed to provide the equivalent retained dose. Thus, for example, a fully retained dose of 150 kBq/kg is equivalent to a complex with a 5 day half-life administered at a dose of 711 kBq/kg. The equivalent administered dose for any appropriate retained doses may be calculated from the biological clearance rate of the complex using methods well known in the art.

Since the decay of one $^{227}$Th nucleus provides one $^{223}$Ra atom, the retention and therapeutic activity of the $^{227}$Th will be directly related to the $^{223}$Ra dose suffered by the patient. The amount of $^{223}$Ra generated in any particular situation can be calculated using well known methods.

In a preferred embodiment, the present invention therefore provides a method for the treatment of disease in a mammalian subject (as described herein), said method comprising administering to said subject a therapeutically effective quantity of at least one tissue-targeting thorium complex as described herein.

It is obviously desirable to minimise the exposure of a subject to the $^{223}$Ra daughter isotope, unless the properties of this are usefully employed. In particular, the amount of radium-223 generated in vivo will typically be greater than 40 kBq/kg, e.g. greater than 60 kBq/Kg. In some cases it will be necessary for the $^{223}$Ra generated in vivo to be more than 80 kBq/kg, e.g. greater than 100 or 115 kBq/kg.

Thorium-227 labelled conjugates in appropriate carrier solutions may be administered intravenously, intracavitary (e.g. intraperitoneally), subcutaneously, orally or topically, as a single application or in a fractionated application regimen. Preferably the complexes conjugated to a targeting moiety will be administered as solutions by a parenteral (e.g. transcutaneous) route, especially intravenously or by an intracavitary route. Preferably, the compositions of the present invention will be formulated in sterile solution for parenteral administration.

Thorium-227 in the methods and products of the present invention can be used alone or in combination with other treatment modalities including surgery, external beam radiation therapy, chemotherapy, other radionuclides, or tissue temperature adjustment etc. This forms a further, preferred embodiment of the method of the invention and formulations/medicaments may correspondingly comprise at least one additional therapeutically active agent such as another radioactive agent or a chemotherapeutic agent.

In one particularly preferred embodiment the subject is also subjected to stem cell treatment and/or other supportive therapy to reduce the effects of radium-223 induced myelotoxicity.

The thorium (e.g. thorium-227) labelled molecules of the invention may be used for the treatment of cancerous or non-cancerous diseases by targeting disease-related receptors. Typically, such a medical use of $^{227}$Th will be by radioimmunotherapy based on linking $^{227}$Th by a chelator to an antibody, an antibody fragment, or a construct of antibody or antibody fragments for the treatment of cancerous or non-cancerous diseases. The use of $^{227}$Th in methods and pharmaceuticals according to the present invention is particularly suitable for the treatment of breast cancers, gastric cancers, ovarian cancers, non-small-cell lung carcinomas (NSCLC), and uterine cancers.

In a further embodiment of the invention, patients with both soft tissue and skeletal disease may be treated both by the $^{227}$Th and by the $^{223}$Ra generated in vivo by the administered thorium. In this particularly advantageous aspect, an extra therapeutic component to the treatment is derived from the acceptably non-myelotoxic amount of $^{223}$Ra by the targeting of the skeletal disease. In this therapeutic method, $^{227}$Th is typically utilised to treat primary and/or metastatic cancer of soft tissue by suitable targeting thereto and the $^{223}$Ra generated from the $^{227}$Th decay is utilised to treat related skeletal disease in the same subject. This skeletal disease may be metastases to the skeleton resulting from a primary soft-tissue cancer, or may be the primary disease where the soft-tissue treatment is to counter a metastatic cancer. Occasionally the soft tissue and skeletal diseases may be unrelated (e.g. the additional treatment of a skeletal disease in a patient with a rheumatological soft-tissue disease).

Below are provided some example syntheses. The steps shown in these syntheses will be applicable to many embodiments of the present invention. Step a) for example, may proceed via intermediate AGC0021 shown below in many or all of the embodiments described herein.

Synthesis of AGC0020 Key Intermediate
N,N,N'N'-tetrakis(2-aminoethyl)-2-(4-nitrobenzyl)propane-1,3-diamine

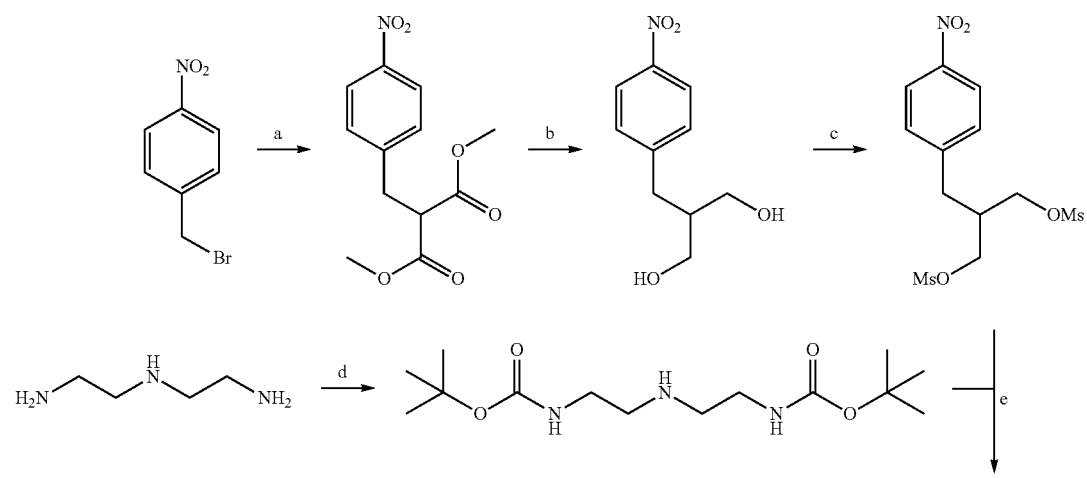

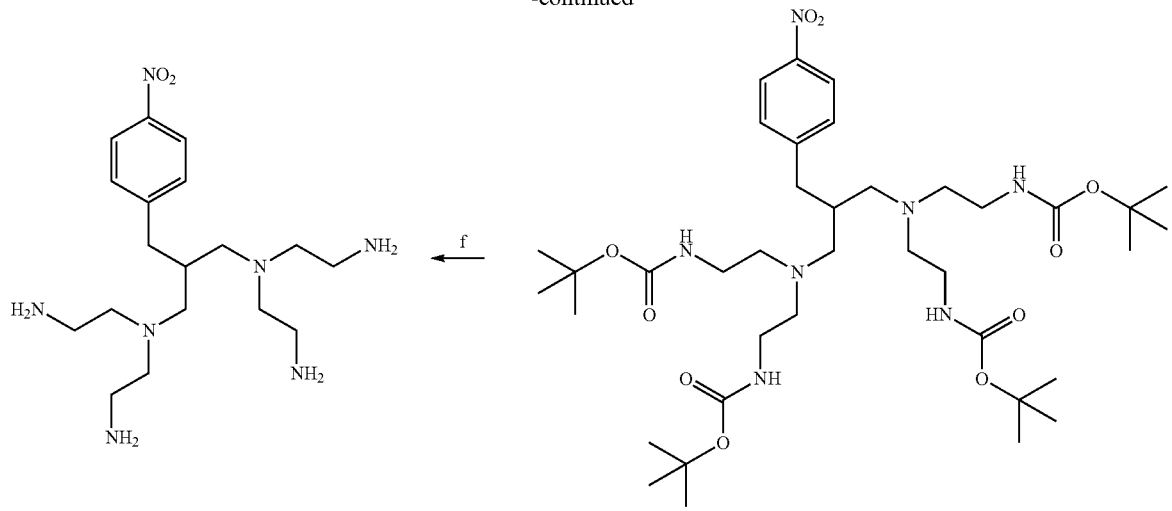

a) Dimethylmalonate, sodium hydride, THF, b) DIBAL—H, THF,
c) MsCl, NEt₃, CH₂Cl₂, d) Imidazole, Boc₂O, CH₂Cl₂, toluene,
e) DIPEA, acetonitrile, f) MeOH, water, AcCl Synthesis of AGC0021 Key Intermediate
3-(benzyloxy)-1-methyl-4-[(2-thioxo-1,3-thiazolidin-3-yl)carbonyl]pyridin-2(1H)-one

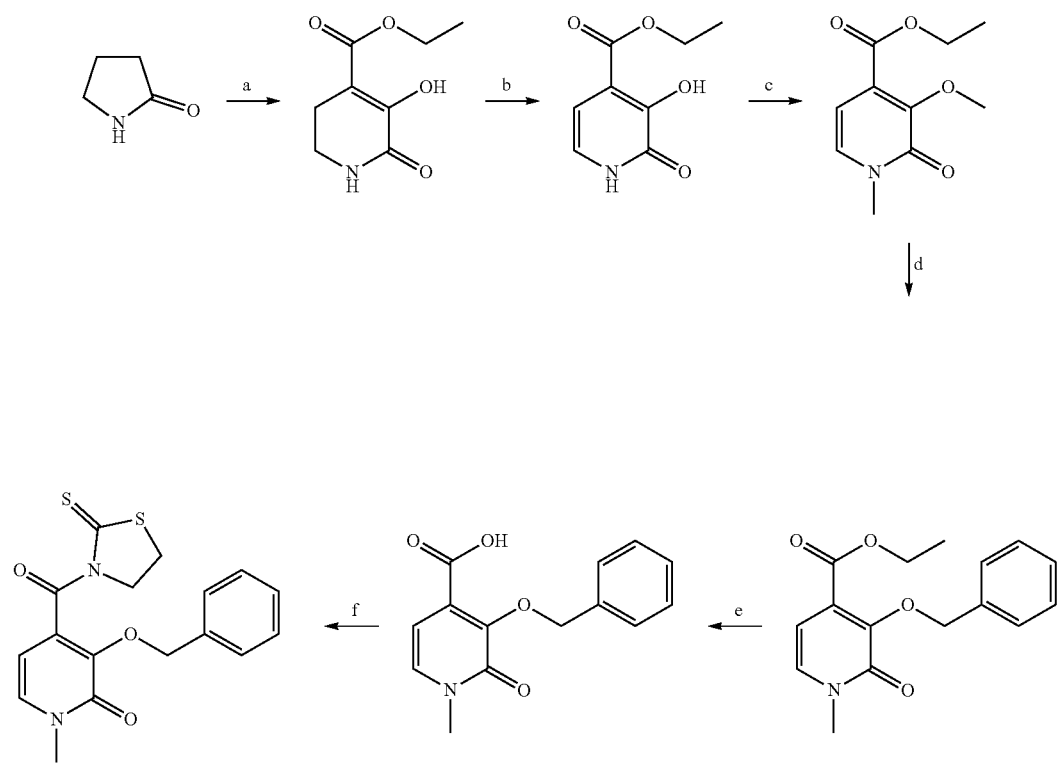

a) Diethyloxalate, potassium ethoxide, toluene, EtOH, b) Pd/C, p-xylene, c) MeI, K₂CO₃, DMSO, acetone,
d) i) BBr₃, DCM, ii) BnBr, K₂CO₃, KI, acetone, e) NaOH, water, MeOH,
f) HS  , DCC, DMAP, DCM

27

Synthesis of chelate of Compound of Formula (VIII)
4-{[4-(3-[bis(2-{[(3-hydroxy-1-methyl-2-oxo-1,2-dihydro-pyridin-4-yl)carbonyl]amino}ethyl)amino]-2-{[bis(2-{[(3- hydroxy-1-methyl-2-oxo-1,2-dihydropyridin-4-yl)carbonyl]amino}ethyl)amino]methyl}propyl)phenyl]amino}-4-oxobutanoic Acid

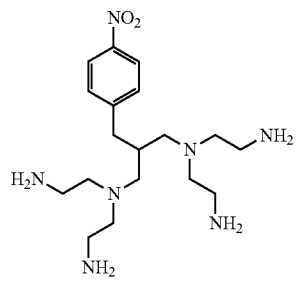

AGC0020
Chemical Formula: $C_{18}H_{35}N_7O_2$
Molecular Weight: 381.52

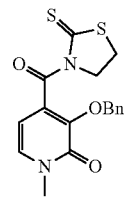

AGC0021
Chemical Formula: $C_{17}H_{16}N_2O_3S_2$
Molecular Weight: 360.45

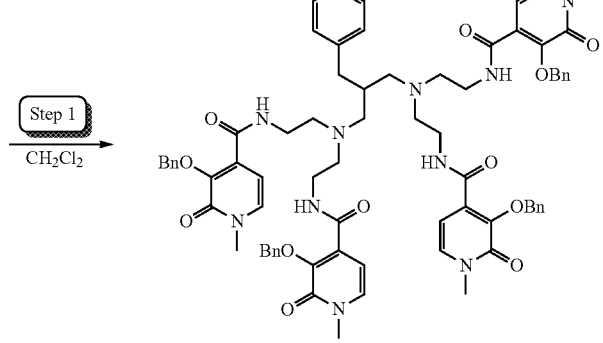

AGC0023
Chemical Formula: $C_{74}H_{79}N_{11}O_{14}$
Molecular Weight: 1346.51

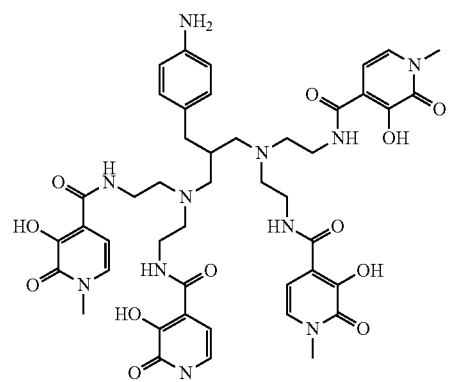

AGC0025
Chemical Formula: $C_{46}H_{57}N_{11}O_{12}$
Molecular Weight: 956.03

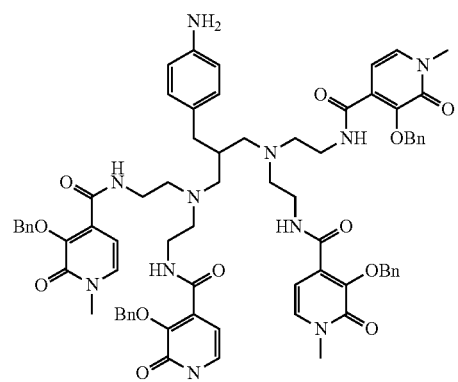

AGC0024
Chemical Formula: $C_{74}H_{81}N_{11}O_{12}$
Molecular Weight: 1316.53

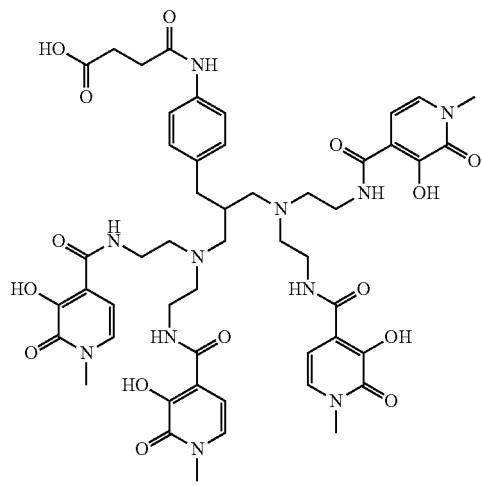

AGC0019
Chemical Formula: $C_{50}H_{61}N_{11}O_{15}$
Molecular Weight: 1056.10

In the methods of formation of the complexes of the present invention, it is preferred that the coupling reaction between the octadentate chelator and the tissue targeting moiety be carried out in aqueous solution. This has several advantages. Firstly, it removes the burden on the manufacturer to remove all solvent to below acceptable levels and certify that removal. Secondly it reduces waste and most importantly it speeds production by avoiding a separation or removal step. In the context of the present radiopharmaceuticals, it is important that synthesis be carried out as rapidly as possible since the radioisotope will be decaying at all times and time spent in preparation wastes valuable material and introduces contaminant daughter isotopes.

Suitable aqueous solutions include purified water and buffers such as any of the many buffers well known in the art. Acetate, citrate, phosphate (e.g. PBS) and sulphonate buffers (such as MES) are typical examples of well-known aqueous buffers.

In one embodiment, the method comprises forming a first aqueous solution of octadentate hydroxypyridinone-containing ligand (as described herein throughout) and a second aqueous solution of a tissue targeting moiety (as described herein throughout) and contacting said first and said second aqueous solutions.

Suitable coupling moieties are discussed in detail above and all groups and moieties discussed herein as coupling and/or linking groups may appropriately be used for coupling the targeting moiety to the ligand. Some preferred coupling groups include amide, ester, ether and amine coupling groups. Esters and amides may conveniently be formed by means of generation of an activated ester groups from a carboxylic acid. Such a carboxylic acid may be present on the targeting moiety, on the coupling moiety and/or on the ligand moiety and will typically react with an alcohol or amine to form an ester or amide. Such methods are very well known in the art and may utilise well known activating reagents including N-hydroxy maleimide, carbodiimide and/or azodicarboxylate activating reagents such as DCC, DIC, EDC, DEAD, DIAD etc.

In a preferred embodiment, the octadentate chelator comprising four hydroxypyridinone moieties, substituted in the N-position with a methyl alkyl group, and a coupling moiety terminating in a carboxylic acid group may be activated using at least one coupling reagent (such as any of those described herein) and an activating agent such as an N-hydroxysuccinimide (NHS) whereby to form the NHS ester of the octadentate chelator. This activated (e.g. NHS) ester may be separated or used without separation for coupling to any tissue targeting moiety having a free amine group (such as on a lysine side-chain). Other activated esters are well known in the art and may be any ester of an effective leaving group, such as fluorinated groups, tosylates, mesylates, iodide etc. NHS esters are preferred, however.

The coupling reaction is preferably carried out over a comparatively short period and at around ambient temperature. Typical periods for the 1-step or 2-step coupling reaction will be around 1 to 240 minutes, preferably 5 to 120 minutes, more preferably 10 to 60 minutes. Typical temperatures for the coupling reaction will be between 0 and 90° C., preferably between 15 and 50° C., more preferably between 20 and 40° C. Around 25° C. or around 38° C. are appropriate.

Coupling of the octadentate chelator to the targeting moiety will typically be carried out under conditions which do not adversely (or at least not irreversibly) affect the binding ability of the targeting moiety. Since the binders are generally peptide or protein based moieties, this requires comparatively mild conditions to avoid denaturation or loss of secondary/tertiary structure. Aqueous conditions (as discussed herein in all contexts) will be preferred, and it will be desirable to avoid extremes of pH and/or redox. Step b) may thus be carried out at a pH between 3 and 10, preferably between 4 and 9 and more preferably between 4.5 and 8. Conditions which are neutral in terms of redox, or very mildly reducing to avoid oxidation in air may be desirable.

A preferred tissue-targeting chelator applicable to all aspects of the invention is AGC0018 as described herein. Complexes of AGC0018 with ions of [227]Th form a preferred embodiment of the complexes of the invention and corresponding formulations, uses, methods etc. Other preferred embodiments usable in all such aspects of the invention include [227]Th complexes of AGC0019 conjugated to tissue targeting moieties (as described herein) including monoclonal antibodies with binding affinity for HER2.

The invention will now be illustrated by the following non-limiting examples. All compounds exemplified in the examples form preferred embodiments of the invention (including preferred intermediates and precursors) and may be used individually or in any combination in any aspect where context allows.

Example 1

Synthesis of a Compound of Formula (III)

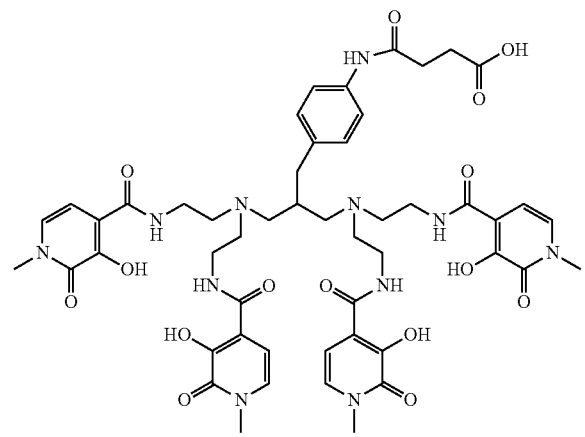

Example 1.1

Synthesis of Dimethyl 2-(4-nitrobenzyl) malonate

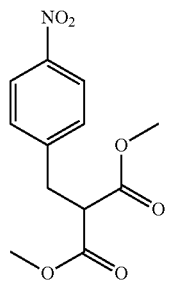

Sodium hydride (60% dispersion, 11.55 g, 289 mmol) was suspended in 450 mL tetrahydrofuran (THF) at 0° C. Dimethyl malonate (40.0 mL, 350 mmol) was added drop wise over approximately 30 minutes. The reaction mixture was stirred for 30 minutes at 0° C. 4-Nitrobenzyl bromide (50.0 g, 231 mmol) dissolved in 150 mL THF was added drop wise over approximately 30 minutes at 0° C., followed by two hours at ambient temperature.

500 mL ethyl acetate (EtOAc) and 250 mL NH$_4$Cl (aq, sat) was added before the solution was filtered. The phases were separated. The aqueous phase was extracted with 2*250 mL EtOAc. The organic phases were combined, washed with 250 mL brine, dried over Na$_2$SO$_4$, filtered and the solvents were removed under reduced pressure. 300 mL heptane and 300 mL methyl tert-butyl ether (MTBE) was added to the residue and heated to 60° C. The solution was filtered. The filtrate was placed in the freezer overnight and filtered. The filter cake was washed with 200 mL heptane and dried under reduced pressure, giving the title compound as an off-white solid.

Yield: 42.03 g, 157.3 mmol, 68%.

1H-NMR (400 MHz, CDCl3): 3.30(d, 2H, 7.8 Hz), 3.68(t, 1H, 7.8 Hz), 3.70(s, 6H), 7.36(d, 2H, 8.7 Hz), 8.13(d, 2H, 8.7 Hz).

Example 1.2

Synthesis of 2-(4-Nitrobenzyl)propane-1,3-diol

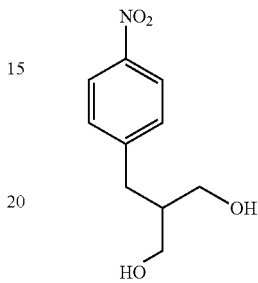

Dimethyl 2-(4-nitrobenzyl) malonate (28.0 g, 104.8 mmol) was dissolved in 560 mL THF at 0° C. Diisobutyl-aluminium hydride (DIBAL-H) (1 M in hexanes, 420 mL, 420 mmol) was added drop wise at 0° C. over approximately 30 minutes. The reaction mixture was stirred for two hours at 0° C.

20 mL water was added drop wise to the reaction mixture at 0° C. 20 mL NaOH (aq, 15%) was added drop wise to the reaction mixture at 0° C. followed by drop wise addition of 20 mL water to the reaction mixture. The mixture was stirred at 0° C. for 20 minutes before addition of approximately 150 g MgSO4. The mixture was stirred at room temperature for 30 minutes before it was filtered on a Büchner funnel. The filter cake was washed with 500 mL EtOAc. The filter cake was removed and stirred with 800 mL EtOAc and 200 mL MeOH for approximately 30 minutes before the solution was filtered. The filtrates were combined and dried under reduced pressure.

DFC on silica using a gradient of EtOAc in heptane, followed by a gradient of MeOH in EtOAc gave the title compound as a pale yellow solid.

Yield: 15.38 g, 72.8 mmol, 69%.

1H-NMR (400 MHz, CDCl3): 1.97-2.13(m, 3H), 2.79(d, 2H, 7.6 Hz), 3.60-3.73(m, 2H), 3.76-3.83 (m, 2H), 7.36(d, 2H, 8.4 Hz), 8.14(d, 2H, 8.4 Hz).

Example 1.3

Synthesis of 2-(4-Nitrobenzyl)propane-1,3-diyl dimethanesulfonate

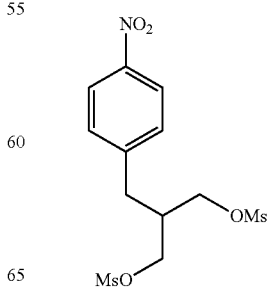

2-(4-nitrobenzyl)propane-1,3-diol (15.3 g, 72.4 mmol) was dissolved in 150 mL CH$_2$Cl$_2$ at 0° C. Triethylamine (23 mL, 165 mmol) was added, followed by methanesulfonyl chloride (12 mL, 155 mmol) drop wise over approximately 15 minutes, followed by stirring at ambient temperature for one hour.

500 mL CH$_2$Cl$_2$ was added, and the mixture was washed with 2*250 mL NaHCO3 (aq, sat), 125 mL HCl (aq, 0.1 M) and 250 mL brine. The organic phase was dried over Na$_2$SO$_4$, filtered and dried under reduced pressure, giving the title compound as an orange solid.

Yield: 25.80 g, 70.2 mmol, 97%.

1H-NMR (400 MHz, CDCl3): 2.44-2.58(m, 1H), 2.87(d, 2H, 7.7 Hz), 3.03(s, 6H), 4.17(dd, 2H, 10.3, 6.0 Hz), 4.26(dd, 2H, 10.3, 4.4 Hz), 7.38(d, 2H, 8.6 Hz), 8.19(d, 2H, 8.6 Hz).

Example 1.4

Synthesis of Di-tert-butyl(azanediylbis(ethane-2,1-diyl))dicarbamate

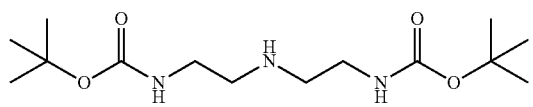 [SMILES: CC(C)(C)OC(=O)NCCNCCNC(=O)OC(C)(C)C]

Imidazole (78.3 g, 1.15 mol) was suspended in 500 mL CH$_2$Cl$_2$ at room temperature. Di-tert-butyl dicarbonate (Boc$_2$O) (262.0 g, 1.2 mol) was added portion wise. The reaction mixture was stirred for one hour at room temperature. The reaction mixture was washed with 3*750 mL water, dried over Na$_2$SO$_4$, filtered and the volatiles were removed under reduced pressure.

The residue was dissolved in 250 mL toluene and diethylenetriamine (59.5 mL, 550 mmol) was added. The reaction mixture was stirred for two hours at 60° C. 1 L CH$_2$Cl$_2$ was added, and the organic phase was washed with 2*250 mL water. The organic phase was dried over Na$_2$SO$_4$, filtered and reduced under reduced pressure. DFC on silica using a gradient of methanol (MeOH) in CH$_2$Cl$_2$ with triethylamine gave the title compound as a colorless solid.

Yield: 102 g, 336 mmol, 61%.

$^1$H-NMR (400 MHz, CDCl3): 1.41(s, 18H), 1.58(bs, 1H), 2.66-2.77(m, 4H), 3.13-3.26(m, 4H), 4.96(bs, 2H).

Example 1.5

Synthesis of Tetra-tert-butyl (((2-(4-nitrobenzyl)propane-1,3-diyl)bis(azanetriyl))tetrakis(ethane-2,1-diyl))tetracarbamate

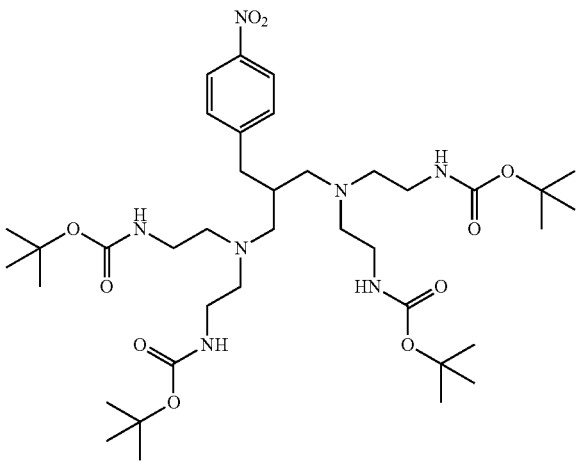 [SMILES: CC(C)(C)OC(=O)NCCN(CCNC(=O)OC(C)(C)C)CC(Cc1ccc([N+](=O)[O-])cc1)CN(CCNC(=O)OC(C)(C)C)CCNC(=O)OC(C)(C)C]

2-(4-Nitrobenzyl)propane-1,3-diyl dimethanesulfonate (26.0 g, 71 mmol) and di-tert-butyl(azanediylbis(ethane-2,1-diyl))dicarbamate (76.0 g, 250 mmol) were dissolved in 700 mL acetonitrile. N,N-diisopropylethylamine (43 mL, 250 mmol) was added. The reaction mixture was stirred for 4 days at reflux.

The volatiles were removed under reduced pressure.

DFC on silica using a gradient of EtOAc in heptane gave the tile compound as pale yellow solid foam.

Yield: 27.2 g, 34.8 mmol, 49%.

$^1$H-NMR (400 MHz, CDCl3): 1.40(s, 36H), 1.91-2.17(m, 3H), 2.27-2.54(m, 10H), 2.61-2.89(m, 2H), 2.98-3.26(m, 8H), 5.26(bs, 4H), 7.34(d, 2H, 8.5 Hz), 8.11(d, 2H, 8.5 Hz).

Example 1.6

Synthesis of N$^1$,N$^{1'}$-(2-(4-nitrobenzyl)propane-1,3-diyl)bis(N$^1$-(2-aminoethyl)ethane-1,2-diamine), AGC0020

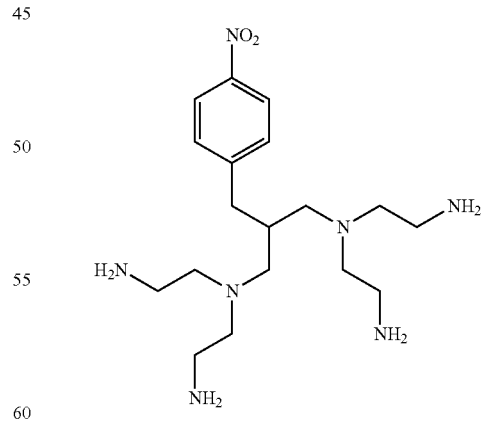

Tetra-tert-butyl (((2-(4-nitrobenzyl)propane-1,3-diyl)bis(azanetriyl))tetrakis(ethane-2,1-diyl))tetracarbamate (29.0 g, 37.1 mmol) was dissolved in 950 mL MeOH and 50 mL water. Acetyl chloride (50 mL, 0.7 mol) was added drop wise over approximately 20 minutes at 30° C. The reaction mixture was stirred overnight.

The volatiles were removed under reduced pressure and the residue was dissolved in 250 mL water. 500 mL CH$_2$Cl$_2$ was added, followed by 175 mL NaOH (aq, 5 M, saturated with NaCl). The phases were separated, and the aqueous phase was extracted with 4*250 mL CH$_2$Cl$_2$. The organic phases were combined, dried over Na$_2$SO$_4$, filtered and dried under reduced pressure, giving the title compound as viscous red brown oil.

Yield: 11.20 g, 29.3 mmol, 79%. Purity (HPLC FIG. 9): 99.3%.

$^1$H-NMR (300 MHz, CDCl$_3$): 1.55(bs, 8H), 2.03(dt, 1H, 6.6, 13.3 Hz), 2.15(dd, 2H, 12.7, 6.6), 2.34-2.47(m, 10H), 2.64-2.77(m, 10H), 7.32(d, 2H, 8.7 Hz), 8.10(d, 2H, 8.7 Hz).

$^{13}$C-NMR (75 MHz, CDCl$_3$): 37.9, 38.5, 39.9, 58.0, 58.7, 123.7, 130.0, 146.5, 149.5

Example 1.7

Synthesis of Ethyl 5-hydroxy-6-oxo-1,2,3,6-tetrahydropyridine-4-carboxylate

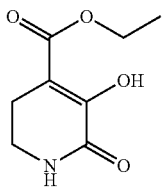

2-pyrrolidinone (76 mL, 1 mol) and diethyl oxalate (140 mL, 1.03 mol) was dissolved in 1 L toluene at room temperature. Potassium ethoxide (EtOK) (24% in EtOH, 415 mL, 1.06 mol) was added, and the reaction mixture was heated to 90° C. 200 mL EtOH was added portion wise during the first hour of the reaction due to thickening of the reaction mixture. The reaction mixture was stirred overnight and cooled to room temperature. 210 mL HCl (5 M, aq) was added slowly while stirring. 200 mL brine and 200 mL toluene was added, and the phases were separated.

The aqueous phase was extracted with 2×400 mL CHCl$_3$. The combined organic phases were dried (Na$_2$SO$_4$), filtered and reduced in vacuo. The residue was recrystallized from EtOAc, giving the title compound as a pale yellow solid.

Yield: 132.7 g, 0.72 mol, 72%.

Example 1.8

Synthesis of Ethyl 3-hydroxy-2-oxo-1,2-dihydropyridine-4-carboxylate

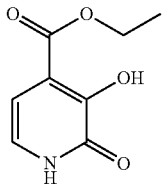

{Ethyl 5-hydroxy-6-oxo-1,2,3,6-tetrahydropyridine-4-carboxylate} (23.00 g, 124.2 mmol) was dissolved in 150 mL p-xylene and Palladium on carbon (10%, 5.75 g) was added. The reaction mixture was stirred at reflux over night. After cooling to room temperature, the reaction mixture was diluted with 300 mL MeOH and filtered through a short pad of Celite®. The pad was washed with 300 mL MeOH. The solvents were removed in vacuo, giving the title compound as a pale red-brownish solid.

Yield: 19.63 g, 107.1 mmol, 86%. MS (ESI, pos): 206.1 [M+Na]$^+$, 389.1[2M+Na]$^+$

Example 1.9

Synthesis of Ethyl 3-methoxy-1-methyl-2-oxo-1,2-dihydropyridine-4-carboxylate

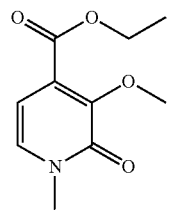

{ethyl 3-hydroxy-2-oxo-1,2-dihydropyridine-4-carboxylate} (119.2 g, 0.65 mol) was dissolved in 600 mL dimethyl sulfoxide (DMSO) and 1.8 L acetone at room temperature. K$_2$CO$_3$ (179.7 g, 1.3 mol) was added. Methyl iodide (MeI) (162 mL, 321 mmol) dissolved in 600 mL acetone was added drop wise over approximately 1 hour at room temperature.

The reaction mixture was stirred for an additional two hours at room temperature before MeI (162 mL, 2.6 mol) was added. The reaction mixture was stirred at reflux overnight. The reaction mixture was reduced under reduced pressure and 2.5 L EtOAc was added.

The mixture was filtered and reduced under reduced pressure. Purification by dry flash chromatography (DFC) on SiO$_2$ using a gradient of EtOAc in heptane gave the title compound.

Yield: 56.1 g, 210.1 mmol, 32%. MS (ESI, pos):234.1 [M+Na]$^+$, 445.1[2M+Na]$^+$

Example 1.10

Synthesis of Ethyl 3-(benzyloxy)-1-methyl-2-oxo-1,2-dihydropyridine-4-carboxylate

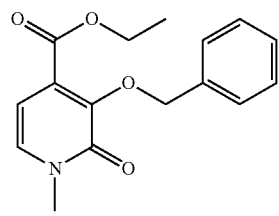 [SMILES: CCOC(=O)c1ccn(C)c(=O)c1OCc1ccccc1]

{ethyl 3-methoxy-1-methyl-2-oxo-1,2-dihydropyridine-4-carboxylate} (5.93 g, 28.1 mmol) was dissolved in 80 mL dichlormethane (DCM) at −78° C. and BBr$_3$ (5.3 mL, 56.2 mmol) dissolved in 20 mL DCM was added drop wise. The reaction mixture was stirred for 1 hour at −78° C. before heating the reaction to 0° C. The reaction was quenched by drop wise addition of 25 mL tert-butyl methyl ether (tert-BuOMe) and 25 mL MeOH.

The volatiles were removed in vacuo. The residue was dissolved in 90 mL DCM and 10 mL MeOH and filtered through a short pad of SiO$_2$. The pad was washed with 200 mL 10% MeOH in DCM. The volatiles were removed in vacuo. The residue was dissolved in 400 mL acetone. K$_2$Co$_3$ (11.65 g, 84.3 mmol), KI (1.39 g, 8.4 mmol) and benzyl bromide (BnBr) (9.2 mL, 84.3 mmol) were added. The reaction mixture was stirred at reflux overnight. The reaction mixture was diluted with 200 mL EtOAc and washed with 3×50 mL water and 50 mL brine. The combined aqueous phases were extracted with 2×50 mL EtOAc. The combined organic phases were dried (Na$_2$SO$_4$), filtered, and the volatiles were removed in vacuo and purified by dry flash chromatography on SiO$_2$ using EtOAc (40-70%) in heptanes as the eluent to give the title compound.

Yield: 5.21 g, 18.1 mmol, 65%. MS (ESI, pos): 310.2 [M+Na]$^+$, 597.4[2M+Na]$^+$ Example 1.11

Synthesis of 3-(Benzyloxy)-1-methyl-2-oxo-1,2-dihydropyridine-4-carboxylic Acid

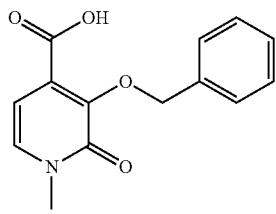 [SMILES: Cn1ccc(C(=O)O)c(OCc2ccccc2)c1=O]

{ethyl 3-(benzyloxy)-1-methyl-2-oxo-1,2-dihydropyridine-4-carboxylate} (27.90 g, 97.1 mmol) was dissolved in 250 mL MeOH and 60 mL NaOH (5M, aq) was added. The reaction mixture was stirred for 2 hours at room temperature before the reaction mixture was concentrated to approximately ⅓ in vacuo. The residue was diluted with 150 mL water and acidified to pH 2 using hydrogen chloride (HCl) (5M, aq). The precipitate was filtered and dried in vacuo, giving the title compound as a colorless solid. Yield: 22.52 g, 86.9 mmol, 89%.

Example 1.12

Synthesis of 3-(Benzyloxy)-1-methyl-4-(2-thioxothiazolidine-3-carbonyl)pyridine-2(1H)-one (AGC0021)

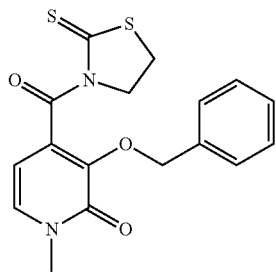 [SMILES: Cn1ccc(C(=O)N2CCSC2=S)c(OCc2ccccc2)c1=O]

{3-(benzyloxy)-1-methyl-2-oxo-1,2-dihydropyridine-4-carboxylic acid} (3.84 g, 14.8 mmol), 4-dimethylaminopyridine (DMAP) (196 mg, 1.6 mmol) and 2-thiazoline-2-thiol (1.94 g, 16.3 mmol) was dissolved in 50 mL DCM. N,N'-Dicyclohexylcarbodiimide (DCC) (3.36 g, 16.3 mmol) was added. The reaction mixture was stirred over night. The reaction was filtered, the solids washed with DCM and the filtrate was reduced in vacuo. The resulting yellow solid was recrystallized from isopropanol/DCM, giving AGC0021. Yield: 4.65 g, 12.9 mmol, 87%. MS(ESI, pos): 383[M+Na]$^+$, 743[2M+Na]$^+$ Example 1.13

Synthesis of AGC0023

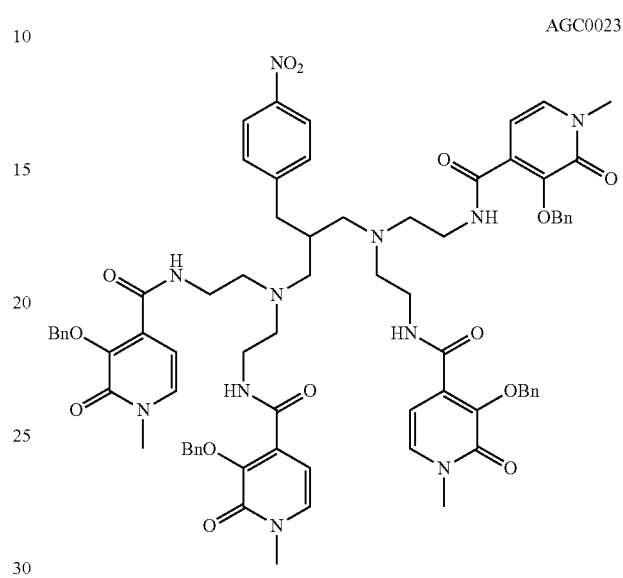

AGC0020 (8.98 g; 23.5 mmol) was dissolved in CH$_2$Cl$_2$ (600 mL). AGC0021 (37.43 g; 103.8 mmol) was added. The reaction was stirred for 20 hours at room temperature. The reaction mixture was concentrated under reduced pressure.

DFC on SiO$_2$ using a gradient of methanol in a 1:1 mixture of EtOAc and CH$_2$Cl$_2$ yielded AGC0023 as a solid foam.

Average yield: 26.95 g, 20.0 mmol, 85%.

Example 1.14

Synthesis of AGC0024

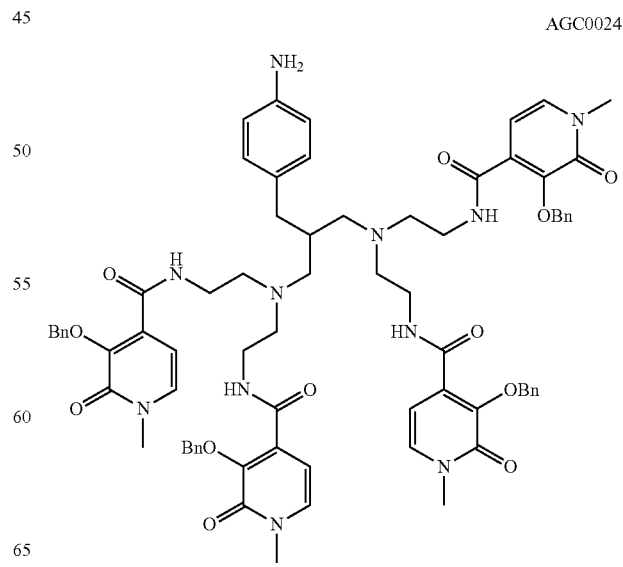

AGC0023 (26.95 g; 20.0 mmol) was dissolved in ethanol (EtOH) (675 mL). Iron (20.76 g; 0.37 mol) and NH$_4$Cl (26.99 g; 0.50 mol) were added, followed by water (67 mL). The reaction mixture was stirred at 70° C. for two hours. More iron (6.75 g; 121 mmol) was added, and the reaction mixture was stirred for one hour at 74° C. More iron (6.76 g; 121 mmol) was added, and the reaction mixture was stirred for one hour at 74° C. The reaction mixture was cooled before the reaction mixture was reduced under reduced pressure.

DFC on SiO$_2$ using a gradient of methanol in CH$_2$Cl$_2$ yielded AGC0024 as a solid foam.

Yield 18.64 g, 14.2 mmol, 71%.

Example 1.15

Synthesis of AGC0025

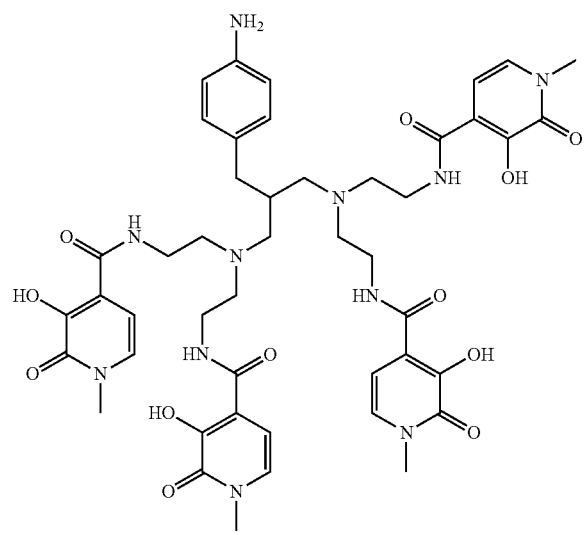

AGC0025

AGC0024 (18.64 g; 14.2 mmol) was dissolved in CH$_2$Cl$_2$ (750 mL) and cooled to 0° C. BBr$_3$ (50 g; 0.20 mol) was added and the reaction mixture was stirred for 75 minutes. The reaction was quenched by careful addition of methanol (MeOH) (130 mL) while stirring at 0° C. The volatiles were removed under reduced pressure. HCl (1.25 M in EtOH, 320 mL) was added to the residue. The flask was then spun using a rotary evaporator at atmospheric pressure and ambient temperature for 15 minutes before the volatiles were removed under reduced pressure.

DFC on non-endcapped C$_{18}$ silica using a gradient of acetonitrile (ACN) in water yielded AGC0025 as a slightly orange glassy solid.

Yield 13.27 g, 13.9 mmol, 98%.

Example 1.16

Synthesis of AGC0019

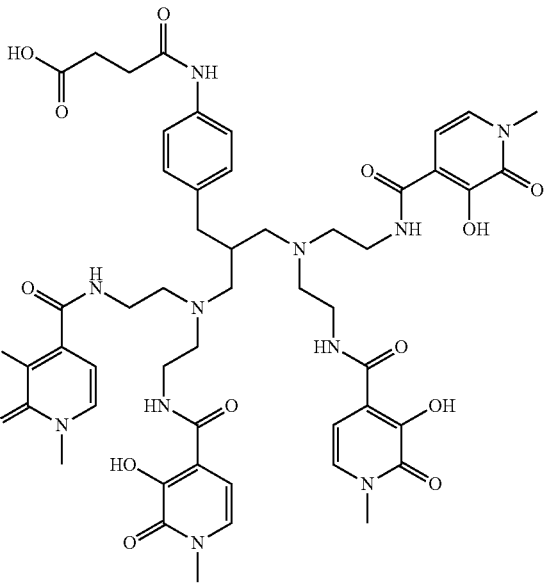

AGC0019

AGC0025 (10.63 g; 11.1 mmol) was dissolved in ACN (204 mL) and water (61 mL) at room temperature. Succinic anhydride (2.17 g; 21.7 mmol) was added and the reaction mixture was stirred for two hours. The reaction mixture was reduced under reduced pressure. DFC on non-endcapped C$_{18}$ silica using a gradient of ACN in water yielded a greenish glassy solid.

The solid was dissolved in MeOH (62 mL) and water (10.6 mL) at 40° C. The solution was added drop wise to EtOAc (750 mL) under sonication. The precipitate was filtered, washed with EtOAc and dried under reduced pressure, giving AGC0019 as an off-white solid with a greenish tinge.

Yield: 9.20 g, 8.7 mmol, 78%. H-NMR (400 MHz, DMSO-d$_6$), $^{13}$C-NMR (100 MHz, DMSO-d$_6$).

Example 2

Isolation of Pure Thorium-227

Thorium-227 is isolated from an actinium-227 generator. Actinium-227 was produced through thermal neutron irradiation of Radium-226 followed by the decay of Radium-227 (t1/2=42.2 m) to Actinium-227. Thorium-227 was selectively retained from an Actinium-227 decay mixture in 8 M HNO$_3$ solution by anion exchange chromatography. A column of 2 mm internal diameter, length 30 mm, containing 70 mg of AG® 1-X8 resin (200-400 mesh, nitrate form) was used. After Actinium-227, Radium-223 and daughters had eluted from the column, Thorium-227 was extracted from the column with 12 M HCl. The eluate containing Thorium-227 was evaporated to dryness and the residue resuspended in 0.01 M HCl prior to labelling step.

Example 3

Example 3.1

Generation of the Monoclonal Antibody to HER2 (AGC1100)

DNA sequences containing the amino acid sequences for the IgGs of the invention were synthesized at Geneart/Life Technologies (Regensburg, Germany) and cloned into a suitable expression vector. All genes were codon optimized for CHO expression. IgGs were expressed either transiently in HEK293 6E cells using the expression system by NRC Canada (Durocher et al., Nucleic Acids Res. 2002 Jan. 15; 30(2):E9) or after stable transfection of CHO-K1 cells. Antibodies were purified via Protein A affinity chromatography and subsequent size exclusion chromatography as previously described (Hristodorov et al., Mol Biotechnol (2013) 53:326-335).

Example 3.2

Coupling of mAb AGC1100 with the Chelator AGC0019 (compound of formula (VIII)) to Give Conjugate AGC1118

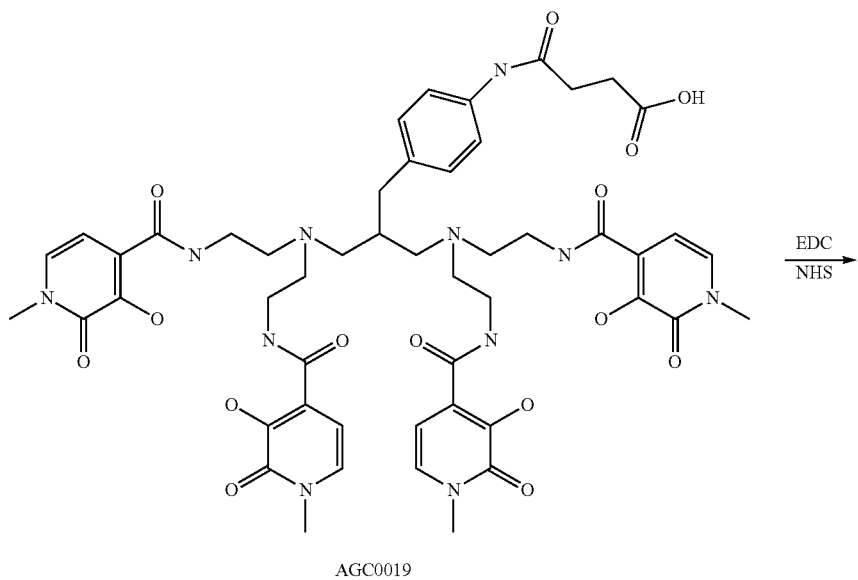

AGC0019

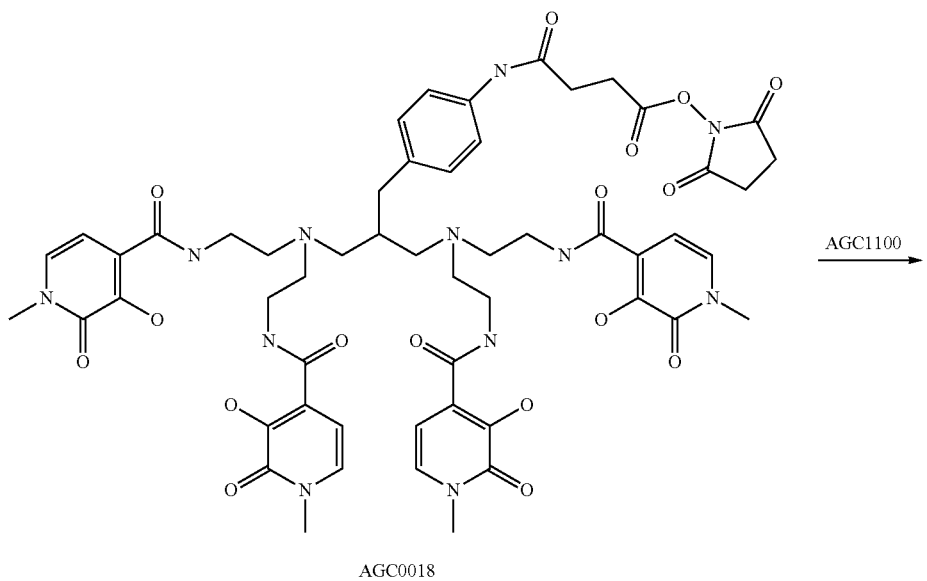

AGC0018

-continued

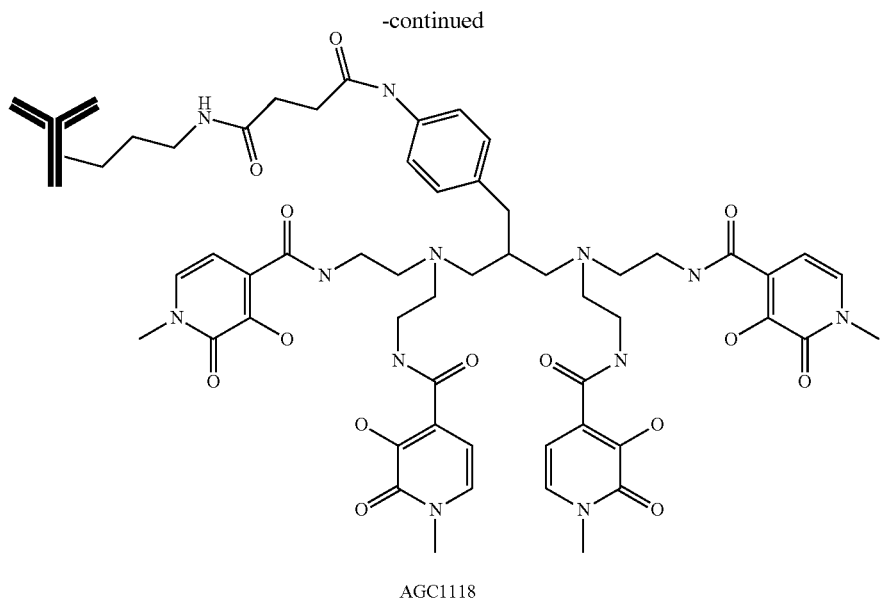

AGC1118

Prior to conjugation, phosphate buffer pH 7.5 is added to the antibody solution (AGC1100) to increase the buffering capacity of the solution. The amount of AGC1100 (mAb) in the vessel is determined.

To trastuzumab in PBS is added 11% 1 M phosphate buffer pH 7.4.

The chelator AGC0019 is dissolved in 1:1, DMA:0.1 M MES buffer pH 5.4. NHS and EDC are dissolved in 0.1 M MES buffer pH 5.4.

A 1/1/3 molar equivalent solution of chelator/N-hydroxysuccinimide (NHS)/1-ethyl-3-(3-dimethylaminopropyl) carbodiimide (EDC) is prepared to activate the chelator.

For conjugation to the antibody a molar ratio of 8/8/25/1 (chelator/NHS/EDC/mAb) of the activated chelator is charged to mAb. After 20-40 minutes, the conjugation reaction is quenched with 12% v/v 0.3M Citric acid to adjust pH to 5.5.

Purification and buffer exchange of AGC0118 conjugates into 30 mM Citrate pH 5.5, 154 mM NaCl are performed by gelfiltration on a Superdex 200 (GE Healthcare) column connected to an ÄKTA system (GE Healthcare). The protein concentration at Abs 280 nm is measured before the product was formulated with buffer (to obtain 2.5 mg/mL AGC0118 in 30 mM citrate, 154 mM NaCl, 2 mM EDTA, 2 mg/mL pABA, pH 5.5). Finally, the solution is filtered through a 0.2 µm filter into sterile bottles prior to storage.

Example 3.3

Preparation of a Dose on $^{227}$Th-AGC0118 Injection

Labelling is performed as previously described:

A vial of 20 MBq thorium-227 chloride film is dissolved in 2 ml 8M HNO3 solution and left for 15 minutes before withdrawing the solution for application to an anion exchange column for removal of radium-223 that has grown in over time. The column is washed with 3 ml 8 M HNO3 and 1 ml water prior to elution of thorium-227 with 3 ml 3M HCl. The eluted activity of thorium-227 is measured and a dose of 10 MBq transferred to an empty 10 ml glass vial. The acid is then evaporated using a vacuum pump and having the vial in a heating block (set to 120° C.) for 30-60 minutes. After reaching room temperature, 6 ml AGC0118 conjugate 2.5 mg/ml is added for radiolabelling. The vial is gently mixed and left for 15 minutes at room temperature. The solution is then sterile filtered into a sterile vial and sample withdrawn for iTLC analysis to determine RCP before use.

Example 3.4

Cytotoxicity of $^{227}$Th-AGC0118 Against SKOV-3 with Different Total Activity

Cell cytotoxicity is tested to various doses of $^{227}$Th-AGC0118 by varying the total activity added to wells during 4 hours incubation time. SKOV-3 cells are seeded 10000 per well in a 96 well plate the day before experiment. A series of total activities 5, 10, 20 and 40 kBq/ml of chelated $^{227}$Th-AGC0118, at specific activity 20 kBq/µg, are added to the cells at day 1. Remaining non-bound $^{227}$Th-AGC0118 is removed by multi array pipette, followed by one additional wash with medium and subsequently fresh culture medium, after the end of incubation period. SKOV-3 cells are cultured in Mc-Coy medium with 10% FBS and 1% Penicillin/Streptomycin. Serum-free medium replaces the culture medium during the incubation with $^{227}$Th-AGC0118. At day four the CellTiter-Glo Luminescent Cell Viability Assay (Promega) is used for measuring cell viability. See FIG. 6.

Example 4

Comparison of Stability of Amide and Isothiocyanate-Linked Conjugates

AGC1118 and the corresponding conjugate having an isothiocyanate coupling moiety (AGC1115) are stored in aqueous solution at 40° C. for 11 days. Samples are taken periodically.

It can be seen from that no measurable decrease in conjugate concentration is seen for the amide-coupled conjugate. In contrast, the isothiocyanate conjugate decreases.

The invention claimed is:

1. A method for the formation of a tissue-targeting thorium complex, said method comprising:
a) forming an octadentate chelator of formula (I) or (II):

(I)

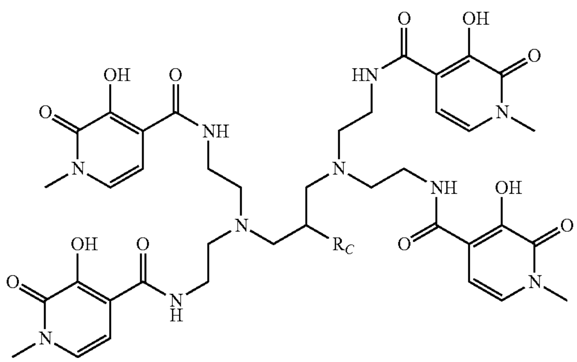

(II)

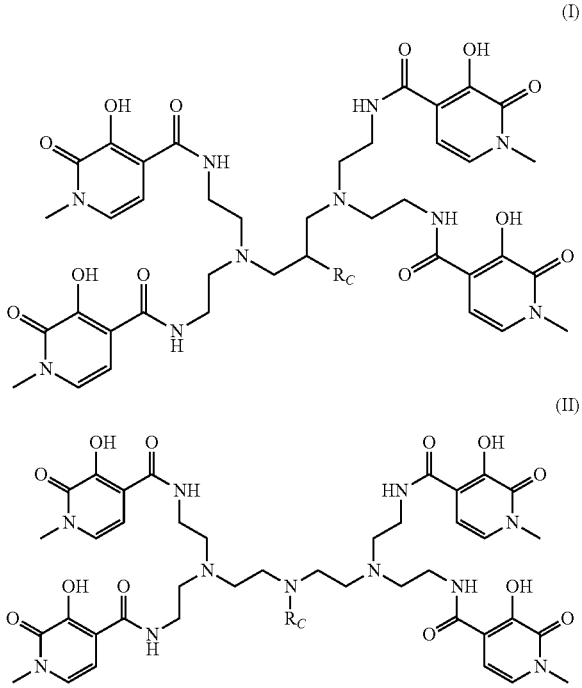

wherein $R_c$ is a moiety selected from the group consisting of a) [—$CH_2$-para phenylene-N(H)—C(=O)—$CH_2$—$CH_2$—C(=O)OH], b) [—$CH_2$—$CH_2$—N(H)—C(=O)—($CH_2$—$CH_2$—O)$_{1\text{-}3}$—$CH_2$—$CH_2$—C(=O)OH], and c) [—$CH_2$-para phenylene-N(H)—C(=O)—($CH_2$)$_{1\text{-}5}$—C(=O)OH];

b) coupling said octadentate chelator to a tissue-targeting moiety comprising a light chain sequence which is SEQ ID No 1 and a heavy chain with sequence similarity or identity of at least 80% with any one of the complete sequences of SEQ ID Nos 2-6:

thereby generating a tissue-targeting chelator; and c) contacting said tissue-targeting chelator with an aqueous solution comprising $4^+$ ions of the alpha-emitting thorium isotope $^{227}$Th, thereby generating the tissue-targeting thorium complex.

2. The method of claim 1 wherein step b) is conducted in aqueous solution.

3. The method of claim 1, wherein step b) further comprises activating the $R_c$ moiety with an amide-coupling reagent; and said amide-coupling reagent is a carbodiimide coupling reagent.

4. The method of claim 1, wherein step b) is conducted in aqueous solution at pH between 4 and 9.

5. The method of claim 1, wherein step b) is conducted between 15 and 50° C. for 5 to 120 minutes.

6. The method of claim 1, wherein step c) is conducted between 15 and 50° C. for 1 to 60 minutes.

7. The method of claim 1, wherein said tissue-targeting moiety comprises a heavy chain with sequence similarity of 98% or more or identity with SEQ ID No 2.

8. The method of claim 3, wherein the carbodiimide coupling reagent is selected from the group consisting of 1-ethyl-3-(3-dimethylaminopropyl)carbodiimid (EDC), N,N'-diisopropylcarbodiimid (DIC), and N,N'-dicyclohexylcarbodiimid (DCC).

9. The method of claim 1, wherein $R_c$ is [—($CH_2$)-para-phenylene-N(H)—C(=O)—($CH_2$)$_2$—C(=O)OH].

* * * * *